US011330994B2

(12) United States Patent
Rogers et al.

(10) Patent No.: US 11,330,994 B2
(45) Date of Patent: May 17, 2022

(54) REDUCED PROFILE FFR CATHETER

(71) Applicant: Medtronic Vascular, Inc., Santa Rosa, CA (US)

(72) Inventors: Ronan Rogers, Galway (IE); Matthew Fleming, Roscommon (IE); Ronan Finn, Galway (IE); Timothy Jones, Galway (IE); Francis McEvoy, Laois (IE); Joshua Hillas, Galway (IE); James Keaveney, Galway (IE); Sean Ward, Dublin (IE); H. Allan Steingisser, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 561 days.

(21) Appl. No.: 15/452,907

(22) Filed: Mar. 8, 2017

(65) Prior Publication Data
US 2018/0256037 A1 Sep. 13, 2018

(51) Int. Cl.
*A61B 5/026* (2006.01)
*A61B 5/0215* (2006.01)
(Continued)

(52) U.S. Cl.
CPC .......... *A61B 5/026* (2013.01); *A61B 5/02158* (2013.01); *A61B 5/6851* (2013.01);
(Continued)

(58) Field of Classification Search
CPC ..... A61B 5/026; A61B 5/6851; A61B 5/6852; A61B 5/02158; A61M 25/0009;
(Continued)

(56) References Cited

U.S. PATENT DOCUMENTS 4,718,425 A 1/1988 Tanaka et al.
4,771,782 A 9/1988 Millar
(Continued)

FOREIGN PATENT DOCUMENTS

DE 102008045878 3/2010
EP 0263190 10/1986
(Continued)

OTHER PUBLICATIONS

"End." Retrieved from Dictionary.com on May 1, 2020, www.dictionary.com. (Year: 2020).*

*Primary Examiner* — Matthew Kremer
*Assistant Examiner* — Samuel C Kim
(74) *Attorney, Agent, or Firm* — Medler Ferro Woodhouse & Mills PLLC

(57) ABSTRACT

A catheter includes a proximal shaft, a distal shaft, a pressure sensor, and at least one pressure sensor wire. The proximal shaft is substantially C-shaped such that in cross-section, the proximal shaft includes a first circumferential end, a second circumferential end, and a gap between the first circumferential and circumferential end. The proximal shaft defines a groove configured to receive a guidewire therein. The distal shaft is coupled to the proximal shaft and defines a guidewire lumen therein. The pressure sensor is coupled to the distal shaft. The pressure sensor wire is operably connected to the pressure sensor. A proximal portion of the pressure sensor wire is disposed within a proximal shaft wall of the proximal shaft and a distal portion of the pressure sensor wire is disposed within a distal shaft wall of the distal shaft.

16 Claims, 23 Drawing Sheets

(51) Int. Cl.
  *A61B 5/00* (2006.01)
  *A61M 25/00* (2006.01)
  *A61M 25/01* (2006.01)
(52) U.S. Cl.
  CPC .................. *A61B 5/6852* (2013.01); *A61M 2025/0002* (2013.01); *A61M 2025/0042* (2013.01); *A61M 2025/0047* (2013.01); *A61M 2025/0177* (2013.01)
(58) Field of Classification Search
  CPC .......... A61M 25/0021; A61M 25/0045; A61M 2025/0042; A61M 2025/0046
  See application file for complete search history.

(56) References Cited

U.S. PATENT DOCUMENTS

| | | | |
|---|---|---|---|
| 4,796,641 A | 1/1989 | Mills et al. | |
| 4,815,472 A | 3/1989 | Wise et al. | |
| 4,850,358 A | 7/1989 | Millar | |
| 4,901,731 A | 2/1990 | Millar | |
| 4,924,877 A | 5/1990 | Brooks | |
| 4,928,693 A | 5/1990 | Goodin et al. | |
| 4,936,310 A | 6/1990 | Engstrom et al. | |
| 4,941,473 A | 7/1990 | Tenerz et al. | |
| 4,966,148 A | 10/1990 | Millar | |
| 4,966,156 A | 10/1990 | Perry et al. | |
| 5,029,585 A | 7/1991 | Lieber et al. | |
| 5,046,497 A | 9/1991 | Millar | |
| 5,050,297 A | 9/1991 | Metzger | |
| 5,085,223 A | 2/1992 | Lars et al. | |
| 5,125,058 A | 6/1992 | Tenerz et al. | |
| 5,195,375 A | 3/1993 | Tenerz et al. | |
| 5,267,958 A | 12/1993 | Buchbinder et al. | |
| 5,280,786 A | 1/1994 | Wlodarczyk et al. | |
| 5,427,114 A | 6/1995 | Colliver et al. | |
| 5,451,233 A | 9/1995 | Yock | |
| 5,466,222 A | 11/1995 | Ressemann et al. | |
| 5,526,820 A | 6/1996 | Khoury | |
| 5,542,434 A | 8/1996 | Imran et al. | |
| 5,564,425 A | 10/1996 | Tonokura | |
| 5,569,219 A | 10/1996 | Hakki et al. | |
| 5,573,007 A | 11/1996 | Bobo, Sr. | |
| 5,591,129 A | 1/1997 | Shoup et al. | |
| 5,637,091 A | 6/1997 | Hakky et al. | |
| 5,649,909 A * | 7/1997 | Cornelius .......... | A61M 25/0045 604/96.01 |
| RE35,648 E | 11/1997 | Tenerz et al. | |
| 5,694,946 A | 12/1997 | Tenerz et al. | |
| 5,701,905 A | 12/1997 | Esch | |
| 5,715,827 A | 2/1998 | Corl et al. | |
| 5,813,997 A | 9/1998 | Imran et al. | |
| 5,827,243 A | 10/1998 | Palestrant | |
| 5,873,835 A | 2/1999 | Hastings et al. | |
| 5,902,248 A | 5/1999 | Millar et al. | |
| 5,964,714 A | 10/1999 | Lafontaine | |
| 6,033,366 A | 3/2000 | Brockway et al. | |
| 6,056,719 A | 5/2000 | Mickley | |
| 6,089,103 A | 7/2000 | Smith | |
| 6,106,476 A | 8/2000 | Corl et al. | |
| 6,106,486 A | 8/2000 | Tenerz et al. | |
| 6,112,598 A | 9/2000 | Tenerz et al. | |
| 6,142,958 A | 11/2000 | Hammarstrom et al. | |
| 6,167,763 B1 | 1/2001 | Tenerz et al. | |
| 6,182,513 B1 | 2/2001 | Stemme et al. | |
| 6,193,669 B1 | 2/2001 | Degany et al. | |
| 6,224,585 B1 | 5/2001 | Pfeiffer | |
| 6,248,083 B1 | 6/2001 | Smith et al. | |
| 6,296,615 B1 | 10/2001 | Brockway et al. | |
| 6,298,525 B1 * | 10/2001 | Margo .................... | F16L 3/237 24/336 |
| 6,312,380 B1 | 11/2001 | Hoek et al. | |
| 6,336,906 B1 | 1/2002 | Hammarstrom et al. | |
| 6,354,999 B1 | 3/2002 | Dgany et al. | |
| 6,379,308 B1 | 4/2002 | Brockway et al. | |
| 6,394,986 B1 | 5/2002 | Millar | |
| 6,409,677 B1 | 6/2002 | Tulkki | |
| 6,471,656 B1 | 10/2002 | Shalman et al. | |
| 6,517,481 B2 | 2/2003 | Hoek et al. | |
| 6,546,804 B2 | 4/2003 | Stemme et al. | |
| 6,551,250 B2 | 4/2003 | Khalil | |
| 6,565,514 B2 | 5/2003 | Svanerudh et al. | |
| 6,585,660 B2 | 7/2003 | Dorando et al. | |
| 6,615,667 B2 | 9/2003 | Smith | |
| 6,659,957 B1 | 12/2003 | Vardi et al. | |
| 6,659,959 B2 | 12/2003 | Brockway et al. | |
| 6,663,570 B2 | 12/2003 | Mott et al. | |
| 6,716,178 B1 | 4/2004 | Kilpatrick et al. | |
| 6,733,459 B1 * | 5/2004 | Atsumi ................ | A61B 5/0215 600/481 |
| 6,754,608 B2 | 6/2004 | Svanerudh et al. | |
| 6,767,327 B1 | 7/2004 | Corl et al. | |
| 6,821,287 B1 | 11/2004 | Jang | |
| 6,860,851 B2 | 3/2005 | Knudson | |
| 6,868,736 B2 | 3/2005 | Sawatari et al. | |
| 6,926,674 B2 | 8/2005 | Tenerz et al. | |
| 6,938,474 B2 | 9/2005 | Melvangs | |
| 6,966,890 B2 | 11/2005 | Coyle et al. | |
| 6,974,422 B1 | 12/2005 | Millar | |
| 6,976,965 B2 | 12/2005 | Corl et al. | |
| 6,993,974 B2 | 2/2006 | Tenerz et al. | |
| 6,994,695 B1 | 2/2006 | Millar | |
| 7,017,416 B1 | 3/2006 | Liu et al. | |
| 7,021,152 B2 | 4/2006 | Tenerz | |
| 7,025,727 B2 | 4/2006 | Brockway et al. | |
| 7,060,038 B2 | 6/2006 | Letort et al. | |
| 7,097,620 B2 | 8/2006 | Corl et al. | |
| 7,112,170 B2 | 9/2006 | Schock et al. | |
| 7,134,994 B2 | 11/2006 | Alpert et al. | |
| 7,137,953 B2 | 11/2006 | Eigler et al. | |
| 7,211,048 B1 | 5/2007 | Najafi et al. | |
| 7,222,539 B2 | 5/2007 | Tulkki | |
| 7,229,403 B2 | 6/2007 | Schock et al. | |
| 7,245,789 B2 | 7/2007 | Bates et al. | |
| 7,263,894 B2 | 9/2007 | Tenerz | |
| 7,274,956 B2 | 9/2007 | Mott et al. | |
| RE39,863 E | 10/2007 | Smith | |
| 7,294,117 B2 | 11/2007 | Provost-tine et al. | |
| 7,329,223 B1 | 2/2008 | Ainsworth et al. | |
| 7,331,236 B2 | 2/2008 | Smith et al. | |
| 7,343,811 B2 | 3/2008 | Tenerz et al. | |
| 7,347,822 B2 | 3/2008 | Brockway et al. | |
| 7,447,388 B2 | 11/2008 | Bates et al. | |
| 7,450,989 B2 | 11/2008 | Svanerudh | |
| 7,454,244 B2 | 11/2008 | Kassab et al. | |
| 7,458,938 B2 | 12/2008 | Patel et al. | |
| 7,472,601 B1 | 1/2009 | Tenerz et al. | |
| 7,481,774 B2 | 1/2009 | Brockway et al. | |
| 7,527,594 B2 | 5/2009 | Vardi et al. | |
| 7,532,920 B1 | 5/2009 | Ainsworth et al. | |
| 7,599,588 B2 | 10/2009 | Eberle et al. | |
| 7,645,233 B2 | 1/2010 | Tulkki et al. | |
| 7,660,492 B2 | 2/2010 | Bates et al. | |
| 7,724,148 B2 | 5/2010 | Samuelsson et al. | |
| 7,731,664 B1 | 6/2010 | Millar | |
| 7,775,988 B2 | 8/2010 | Pijls | |
| 7,783,338 B2 | 8/2010 | Ainsworth et al. | |
| 7,837,650 B1 | 11/2010 | Cox et al. | |
| 7,875,002 B2 * | 1/2011 | Ricci .................... | A61M 25/104 604/96.01 |
| 7,881,573 B2 | 2/2011 | Eberle et al. | |
| 7,931,603 B2 | 4/2011 | Von Malmborg et al. | |
| 7,946,997 B2 | 5/2011 | Hubinette | |
| 7,967,761 B2 | 6/2011 | Smith | |
| 7,967,762 B2 | 6/2011 | Corl et al. | |
| 7,998,089 B2 | 8/2011 | Smith | |
| 8,025,623 B1 | 9/2011 | Millar | |
| 8,029,447 B2 | 10/2011 | Kanz et al. | |
| 8,059,923 B2 | 11/2011 | Bates et al. | |
| 8,140,146 B2 | 3/2012 | Kim et al. | |
| 8,157,742 B2 | 4/2012 | Taylor | |
| 8,162,856 B2 | 4/2012 | Williams et al. | |
| 8,174,395 B2 | 5/2012 | Samuelsson et al. | |
| 8,187,195 B2 | 5/2012 | Tulkki | |

(56) References Cited

U.S. PATENT DOCUMENTS

| | | |
|---|---|---|
| 8,216,151 B2 | 7/2012 | Smith |
| 8,231,537 B2 | 7/2012 | Ahmed et al. |
| 8,249,815 B2 | 8/2012 | Taylor |
| 8,277,386 B2 | 10/2012 | Ahmed et al. |
| 8,282,565 B2 | 10/2012 | Mahapatra et al. |
| 8,298,156 B2 | 10/2012 | Manstrom et al. |
| 8,311,747 B2 | 11/2012 | Taylor |
| 8,311,748 B2 | 11/2012 | Taylor et al. |
| 8,311,750 B2 | 11/2012 | Taylor |
| 8,315,812 B2 | 11/2012 | Taylor |
| 8,315,813 B2 | 11/2012 | Taylor et al. |
| 8,315,814 B2 | 11/2012 | Taylor et al. |
| 8,317,715 B2 | 11/2012 | Belleville et al. |
| 8,320,723 B2 | 11/2012 | Eberle et al. |
| 8,321,150 B2 | 11/2012 | Taylor |
| 8,410,940 B2 | 4/2013 | Samuelsson et al. |
| 8,419,647 B2 | 4/2013 | Corl et al. |
| 8,419,648 B2 | 4/2013 | Corl et al. |
| 8,461,997 B2 | 6/2013 | Samuelsson et al. |
| 8,485,985 B2 | 7/2013 | Manstrom et al. |
| 8,556,520 B2 | 10/2013 | Elenbaas et al. |
| 8,562,537 B2 | 10/2013 | Alpert et al. |
| 8,636,659 B2 | 1/2014 | Alpert et al. |
| 8,696,584 B2 | 4/2014 | Kassab |
| 8,698,638 B2 | 4/2014 | Samuelsson et al. |
| 8,714,021 B2 | 5/2014 | Gamage |
| 8,797,155 B2 | 8/2014 | Huennekens et al. |
| 8,857,264 B2 | 10/2014 | Gamage |
| 8,958,863 B2 | 2/2015 | Huennekens et al. |
| 8,977,336 B2 | 3/2015 | Huennekens et al. |
| 8,998,823 B2 | 4/2015 | Manstrom et al. |
| 9,011,342 B2 | 4/2015 | Manstrom et al. |
| 9,113,843 B2 | 8/2015 | Manstrom et al. |
| 9,186,072 B2 | 11/2015 | Manstrom et al. |
| 9,220,461 B2 | 12/2015 | Samuelsson et al. |
| 9,259,161 B2 | 2/2016 | Suchecki et al. |
| 9,289,137 B2 | 3/2016 | Corl |
| 9,314,584 B1 | 4/2016 | Riley et al. |
| 9,332,916 B2 | 5/2016 | Kassab |
| 9,339,348 B2 | 5/2016 | Davies et al. |
| 2001/0051769 A1 | 12/2001 | Hoek et al. |
| 2002/0013527 A1 | 1/2002 | Hoek et al. |
| 2002/0035331 A1 | 3/2002 | Brockway et al. |
| 2002/0059827 A1 | 5/2002 | Smith |
| 2002/0065472 A1 | 5/2002 | Brockway et al. |
| 2002/0072880 A1 | 6/2002 | Svanerudh et al. |
| 2002/0143251 A1* | 10/2002 | Richardson ....... A61M 25/0023 600/434 |
| 2002/0157473 A1 | 10/2002 | Stemme et al. |
| 2002/0173724 A1 | 11/2002 | Dorando et al. |
| 2003/0018273 A1 | 1/2003 | Corl et al. |
| 2003/0032886 A1 | 2/2003 | Dgany et al. |
| 2003/0033095 A1 | 2/2003 | Svanerudh et al. |
| 2003/0040674 A1 | 2/2003 | Corl et al. |
| 2003/0120208 A1* | 6/2003 | Houser ............... A61M 25/104 604/103.04 |
| 2003/0159518 A1 | 8/2003 | Sawatari et al. |
| 2003/0163052 A1 | 8/2003 | Mott et al. |
| 2003/0176850 A1 | 9/2003 | Melvas |
| 2003/0195428 A1 | 10/2003 | Brockway et al. |
| 2003/0216621 A1 | 11/2003 | Alpert et al. |
| 2004/0067000 A1 | 4/2004 | Bates et al. |
| 2004/0082844 A1 | 4/2004 | Vardi et al. |
| 2004/0082866 A1 | 4/2004 | Mott et al. |
| 2004/0116816 A1 | 6/2004 | Tenerz et al. |
| 2004/0143240 A1 | 7/2004 | Armstrong et al. |
| 2004/0143261 A1 | 7/2004 | Hartley et al. |
| 2004/0143286 A1* | 7/2004 | Johnson ............ A61M 25/1002 606/194 |
| 2004/0157790 A1 | 8/2004 | Herweijer et al. |
| 2004/0162548 A1 | 8/2004 | Reiser |
| 2004/0167385 A1 | 8/2004 | Rioux et al. |
| 2004/0176790 A1 | 9/2004 | Coyle |
| 2004/0230131 A1 | 11/2004 | Kassab et al. |
| 2004/0254442 A1 | 12/2004 | Williams et al. |
| 2005/0000294 A1 | 1/2005 | Tenerz et al. |
| 2005/0011272 A1 | 1/2005 | Tenerz |
| 2005/0043670 A1 | 2/2005 | Rosenberg |
| 2005/0049451 A1 | 3/2005 | Schock et al. |
| 2005/0187487 A1 | 8/2005 | Azizkhan et al. |
| 2005/0268724 A1 | 12/2005 | Tenerz |
| 2005/0268725 A1 | 12/2005 | Tulkki |
| 2006/0052700 A1 | 3/2006 | Svanerudh |
| 2006/0074318 A1 | 4/2006 | Ahmed et al. |
| 2006/0094966 A1 | 5/2006 | Brockway et al. |
| 2006/0094982 A1 | 5/2006 | Corl et al. |
| 2006/0142756 A1 | 6/2006 | Davies et al. |
| 2006/0207335 A1 | 9/2006 | Tenerz et al. |
| 2006/0241505 A1 | 10/2006 | Ahmed et al. |
| 2006/0287569 A1 | 12/2006 | Schock et al. |
| 2007/0060820 A1 | 3/2007 | Lofgren et al. |
| 2007/0060822 A1 | 3/2007 | Alpert et al. |
| 2007/0078352 A1 | 4/2007 | Pijls |
| 2007/0106142 A1 | 5/2007 | Von Malmborg et al. |
| 2007/0106165 A1 | 5/2007 | Tulkki |
| 2007/0116408 A1 | 5/2007 | Eberle et al. |
| 2007/0133925 A1 | 6/2007 | Bates et al. |
| 2007/0135718 A1 | 6/2007 | Corl et al. |
| 2007/0191717 A1 | 8/2007 | Rosen et al. |
| 2007/0220986 A1 | 9/2007 | Smith et al. |
| 2007/0255144 A1 | 11/2007 | Tulkki et al. |
| 2007/0255145 A1 | 11/2007 | Smith et al. |
| 2008/0119739 A1 | 5/2008 | Vardi et al. |
| 2008/0119758 A1 | 5/2008 | Samuelsson et al. |
| 2008/0132806 A1 | 6/2008 | Smith |
| 2008/0139897 A1 | 6/2008 | Ainsworth et al. |
| 2008/0146993 A1 | 6/2008 | Krishna |
| 2008/0200770 A1 | 8/2008 | Hubinette |
| 2008/0255471 A1 | 10/2008 | Naghavi et al. |
| 2008/0262470 A1 | 10/2008 | Lee et al. |
| 2008/0269572 A1 | 10/2008 | Kanz et al. |
| 2009/0059727 A1 | 3/2009 | Bates et al. |
| 2009/0082678 A1 | 3/2009 | Smith |
| 2009/0088609 A1 | 4/2009 | Schmitz-Rode et al. |
| 2009/0088650 A1 | 4/2009 | Corl |
| 2009/0124880 A1 | 5/2009 | Smith |
| 2009/0125007 A1 | 5/2009 | Splinter |
| 2009/0248049 A1 | 10/2009 | Perkins |
| 2010/0014810 A1 | 1/2010 | Eberle et al. |
| 2010/0087732 A1 | 4/2010 | Eberle et al. |
| 2010/0109104 A1 | 5/2010 | Tlensuu et al. |
| 2010/0113942 A1 | 5/2010 | Eberle |
| 2010/0135111 A1 | 6/2010 | Bates et al. |
| 2010/0152607 A1 | 6/2010 | Kassab |
| 2010/0234698 A1 | 9/2010 | Manstrom et al. |
| 2010/0241008 A1 | 9/2010 | Belleville et al. |
| 2010/0280330 A1 | 11/2010 | Samuelsson et al. |
| 2010/0286536 A1 | 11/2010 | Samuelsson et al. |
| 2010/0286537 A1 | 11/2010 | Pijls |
| 2011/0004198 A1 | 1/2011 | Hoch |
| 2011/0060229 A1 | 3/2011 | Hulvershorn et al. |
| 2011/0066047 A1 | 3/2011 | Belleville et al. |
| 2011/0071407 A1 | 3/2011 | Hubinette et al. |
| 2011/0083521 A1 | 4/2011 | Hollander et al. |
| 2011/0123154 A1 | 5/2011 | Eberle et al. |
| 2011/0137140 A1 | 6/2011 | Tearney et al. |
| 2011/0178383 A1 | 7/2011 | Kassab |
| 2011/0178413 A1 | 7/2011 | Schmitt et al. |
| 2011/0178417 A1 | 7/2011 | Kassab |
| 2011/0196255 A1 | 8/2011 | Kassab |
| 2011/0245693 A1 | 10/2011 | Hastings et al. |
| 2011/0251497 A1 | 10/2011 | Corl et al. |
| 2011/0306867 A1 | 12/2011 | Gopinathan et al. |
| 2011/0319773 A1 | 12/2011 | Kanz et al. |
| 2012/0053918 A1 | 3/2012 | Taylor |
| 2012/0071782 A1 | 3/2012 | Patil et al. |
| 2012/0072190 A1 | 3/2012 | Sharma et al. |
| 2012/0101355 A1 | 4/2012 | Gopinathan et al. |
| 2012/0101369 A1 | 4/2012 | Patil et al. |
| 2012/0108943 A1 | 5/2012 | Bates et al. |
| 2012/0136244 A1 | 5/2012 | Manstrom et al. |
| 2012/0172731 A1 | 7/2012 | Smith |
| 2012/0172732 A1 | 7/2012 | Meyer |
| 2012/0203118 A1 | 8/2012 | Samuelsson et al. |

(56) References Cited

U.S. PATENT DOCUMENTS

| | | |
|---|---|---|
| 2012/0220836 A1 | 8/2012 | Alpert et al. |
| 2012/0220837 A1 | 8/2012 | Alpert et al. |
| 2012/0220883 A1 | 8/2012 | Manstrom et al. |
| 2012/0227505 A1 | 9/2012 | Belleville et al. |
| 2012/0271178 A1 | 10/2012 | Smith |
| 2012/0278008 A1 | 11/2012 | Davies et al. |
| 2012/0316419 A1 | 12/2012 | Chevalier |
| 2013/0015975 A1 | 1/2013 | Huennekens et al. |
| 2013/0023762 A1 | 1/2013 | Huennekens et al. |
| 2013/0023763 A1 | 1/2013 | Huennekens et al. |
| 2013/0046190 A1 | 2/2013 | Davies |
| 2013/0060133 A1 | 3/2013 | Kassab et al. |
| 2013/0090555 A1 | 4/2013 | Kassab |
| 2013/0096409 A1 | 4/2013 | Hiltner et al. |
| 2013/0109980 A1 | 5/2013 | Teo |
| 2013/0116579 A1 | 5/2013 | Svanerudh |
| 2013/0131523 A1 | 5/2013 | Suchecki et al. |
| 2013/0172855 A1* | 7/2013 | Wood ............ A61M 25/09 604/528 |
| 2013/0190633 A1 | 7/2013 | Dorando et al. |
| 2013/0303914 A1 | 11/2013 | Hiltner et al. |
| 2013/0324864 A1 | 12/2013 | Manstrom et al. |
| 2014/0024235 A1 | 1/2014 | Russell |
| 2014/0024950 A1 | 1/2014 | Hiltner et al. |
| 2014/0086461 A1 | 3/2014 | Yao et al. |
| 2014/0180140 A1 | 6/2014 | Alpert |
| 2014/0187980 A1 | 7/2014 | Burkett |
| 2014/0187984 A1 | 7/2014 | Burkett |
| 2014/0276142 A1 | 9/2014 | Dorando |
| 2014/0379269 A1 | 12/2014 | Schmitt |
| 2015/0032011 A1 | 1/2015 | McGowan et al. |
| 2015/0105673 A1 | 4/2015 | Gregorich |
| 2015/0112191 A1 | 4/2015 | Gilboa et al. |
| 2015/0141853 A1 | 5/2015 | Miller et al. |
| 2015/0148693 A1 | 5/2015 | Burkett |
| 2015/0157216 A1 | 6/2015 | Stigall et al. |
| 2015/0173722 A1 | 6/2015 | Huennekens et al. |
| 2015/0223707 A1 | 8/2015 | Ludoph |
| 2015/0265167 A1 | 9/2015 | McGowan et al. |
| 2015/0272449 A1 | 10/2015 | Meyer |
| 2015/0282765 A1 | 10/2015 | Goshen et al. |
| 2015/0313479 A1 | 11/2015 | Stigall et al. |
| 2015/0359438 A1* | 12/2015 | McCaffrey ............ A61B 5/0215 600/486 |
| 2015/0359439 A1 | 12/2015 | Manstrom et al. |
| 2016/0022153 A1 | 1/2016 | Dorando |
| 2016/0066802 A1 | 3/2016 | Keller |
| 2016/0106321 A1 | 4/2016 | Sharma et al. |

FOREIGN PATENT DOCUMENTS

| | | |
|---|---|---|
| EP | 1658808 | 8/1995 |
| EP | 1260175 | 11/2002 |
| EP | 1419796 | 5/2004 |
| EP | 1493381 | 1/2005 |
| EP | 1514512 | 3/2005 |
| EP | 1702641 | 9/2006 |
| JP | 10033488 | 10/1998 |
| JP | 2000333913 | 12/2000 |
| JP | 2004-194996 | 7/2004 |
| JP | 2005095603 | 4/2005 |
| JP | 20053638066 | 4/2005 |
| JP | 20053705458 | 10/2005 |
| JP | 2006204378 | 8/2006 |
| JP | 10137199 | 5/2010 |
| NL | 2009285 | 8/2012 |
| WO | WO1997/000641 | 1/1997 |
| WO | WO1999/058059 | 11/1999 |
| WO | WO2003/022122 | 3/2003 |
| WO | WO2006/037082 | 4/2006 |
| WO | WO2006/0117154 | 11/2006 |
| WO | WO2011/0120565 | 10/2011 |
| WO | WO2011/0161212 | 12/2011 |
| WO | WO2012/093260 | 7/2012 |
| WO | WO2012/173697 | 12/2012 |
| WO | WO2013/061281 | 5/2013 |
| WO | WO2014/025255 | 2/2014 |
| WO | WO2014/176448 | 10/2014 |
| WO | WO2015/150128 | 10/2015 |
| WO | WO2016/001017 | 1/2016 |

* cited by examiner

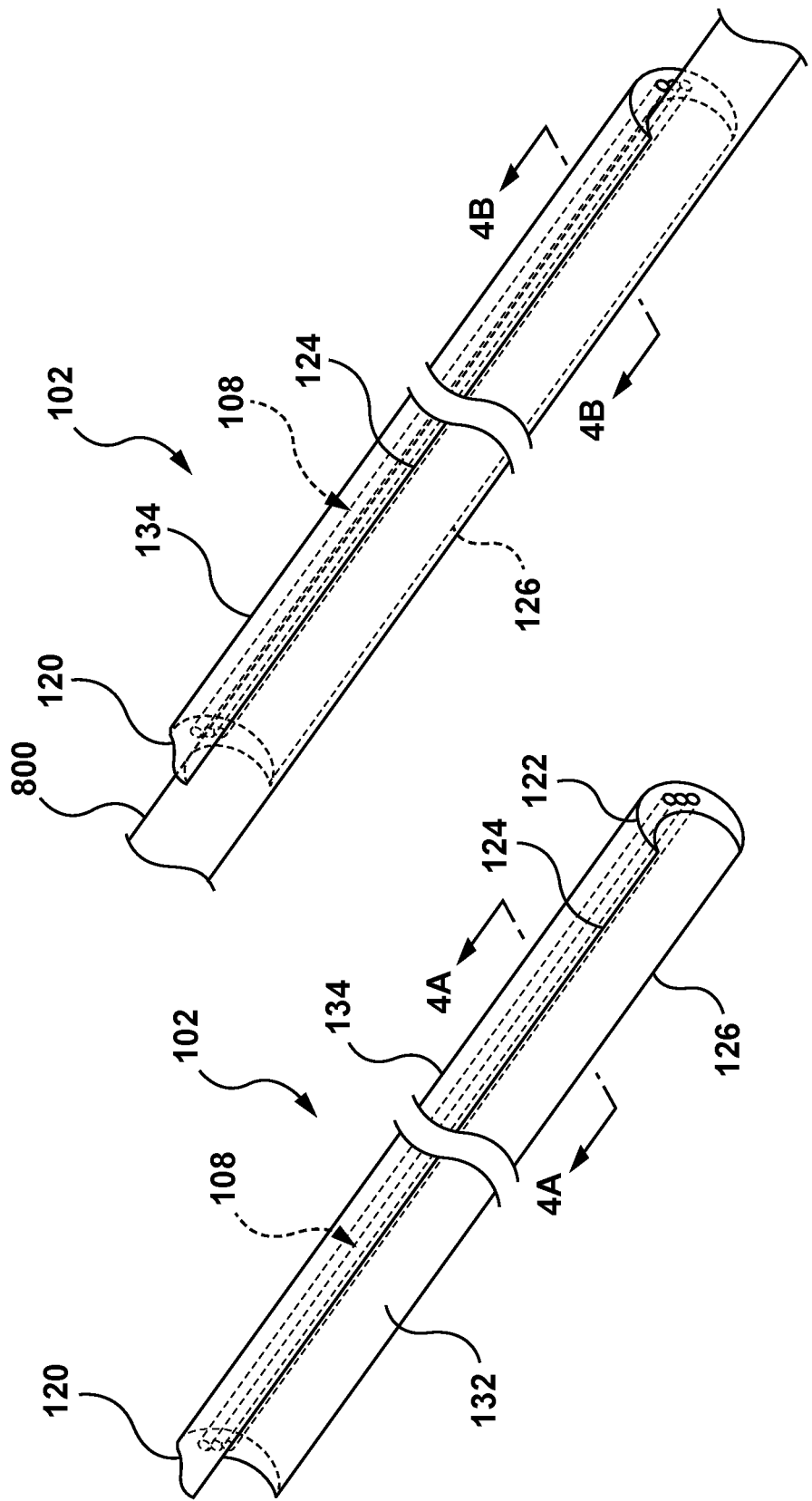

REDUCED PROFILE FFR CATHETER

FIELD OF THE INVENTION

The present invention relates to systems for calculating a Fractional Flow Reserve. More particularly, the present invention relates to catheters to improve the accuracy of Fractional Flow Reserve calculations.

BACKGROUND OF THE INVENTION

The severity of a stenosis or lesion in a blood vessel may be assessed by obtaining proximal and distal pressure measurements relative to the given lesion, and using those measurements for calculating a value of a Fractional Flow Reserve (FFR). FFR is defined as the ratio of a distal pressure ($P_d$) measured on a distal side of the lesion to a proximal pressure ($P_a$) measured on a proximal side of the lesion, typically within the aorta (FFR=$P_d/P_a$). Conventionally, a sensor is placed on a distal portion of a guidewire (FFR guidewire) to obtain/measure the distal pressure ($P_d$), while an external pressure transducer is fluidly connected via tubing to a guide catheter for obtaining the proximal, or aortic (AO) pressure ($P_a$). Once the guide catheter is positioned in situ, and the pressure of the blood filling the lumen of the guide catheter is equal to the pressure of the blood at the distal tip of the guide catheter, tubing that fluidly connects the proximal end of the guide catheter to the external pressure transducer also fills with blood such that the external pressure transducer measures the pressure of the blood at the distal tip of the guide catheter. The FFR guidewire is advanced through the guide catheter and through the lesion to a distal side of the lesion. The sensor on the FFR guidewire measures the distal pressure.

Calculation of the FFR value provides a lesion specific index of the functional severity of the lesion in order to determine whether the blockage limits blood flow within the vessel to an extent that treatment is needed. An optimal or normal value of FFR in a healthy vessel is 1.00, while values less than about 0.80 are generally deemed significant and in need of an interventional treatment. Common interventional treatment options include balloon angioplasty and/or stent implantation. If an interventional treatment is required, the interventional device, such as a balloon catheter, is tracked over a guidewire to the site of the lesion. Conventional FFR guidewires generally are not desired by clinicians to be used as guidewires for such interventional devices. Accordingly, if an interventional treatment is required, the clinician generally removes the FFR wire, inserts a conventional guidewire, and tracks the interventional device to the treatment site over the conventional guide wire.

To address this concern, efforts have been made to utilize catheters to take pressure measurements for calculating FFR. Using a catheter (FFR catheter or micro-catheter), a clinician may use a preferred guidewire for tracking the FFR catheter to the site of the lesion. If an interventional treatment is required, the guidewire used with the FFR catheter may remain in situ and the interventional device may be tracked over the existing guidewire to the site of the lesion.

However, such FFR catheters are generally larger in cross-sectional profile than FFR guidewires. Therefore, because the FFR catheter (with a conventional guidewire) or the FFR guidewire extends through the guide catheter, an FFR catheter with a guidewire occupies a larger percentage of the lumen of the guide catheter than a comparatively smaller profile FFR guidewire. Occupying a larger percentage of the guide catheter lumen may affect the accuracy of the measured proximal pressure ($P_a$), which, as explained above, is based on blood filling the lumen of the guide catheter. This error is referred to as dampening of the AO pressure wave. Due to the reduced space between the inner surface of the guide catheter and an outer surface of the proximal portion of the FFR catheter/guidewire combination, the pressure at the distal end of the guide catheter does not propagate proximally through the guide catheter such that changes in the pressure at the distal end are not properly measured by the external pressure transducer. Thus, using a larger profile FFR catheter may introduce errors in the measured proximal pressure ($P_a$). Such errors would then be transferred to the calculation of FFR, which is based in part on the measured proximal pressure.

Accordingly, there is a need for FFR catheters with reduced proximal cross-sectional profiles to minimize AO pressure wave dampening when measuring proximal pressure ($P_a$), thereby enabling a more accurate FFR calculation.

BRIEF SUMMARY OF THE INVENTION

Embodiments hereof relate to a catheter including a proximal shaft, a distal shaft, a pressure sensor, and a pressure sensor wire. The proximal shaft is substantially C-shaped such that in cross-section, the proximal shaft includes a first circumferential end, a second circumferential end, and a gap between the first circumferential end and the second circumferential end. The proximal shaft defines a groove configured to receive a guidewire therein. The distal shaft is coupled to the proximal shaft and defines a guidewire lumen therein. The pressure sensor is coupled to the distal shaft. The pressure sensor wire is operably connected to the pressure sensor. A proximal portion of the pressure sensor wire is disposed within a proximal shaft wall of the proximal shaft and a distal portion of the pressure sensor wire is disposed within a distal shaft wall of the distal shaft.

Embodiments hereof also relate to a catheter including a proximal pushwire, a distal shaft, a pressure sensor, and a pressure sensor wire. The distal shaft is coupled to the proximal pushwire and defines a guidewire lumen and a wire lumen. The pressure sensor is coupled to the distal shaft. The pressure sensor wire is operably connected to the pressure sensor. A proximal portion of the pressure sensor wire is attached to an outer surface of the proximal pushwire and a distal portion of the pressure sensor wire extends through the wire lumen of the distal shaft.

Embodiments hereof also relate to a method of forming a catheter. The method includes attaching a proximal portion of a pressure wire to an outer surface of a proximal pushwire. The pressure wire extends distally of a distal end of the proximal pushwire. The method further includes locating a first shaft adjacent a distal portion of the pressure wire. The method further includes locating a second shaft around the first shaft and the distal portion of the pressure wire, and heat shrinking the second shaft such that the second shaft shrinks to tightly fit against an outer surface of the first shaft and the distal portion of the pressure wire. The method may further include operatively connecting the pressure sensor wire to a pressure sensor disposed on a distal portion of the first shaft.

BRIEF DESCRIPTION OF DRAWINGS

FIG. 3A is a perspective illustration of an embodiment of a proximal shaft of the FFR catheter of FIG. 1.

FIG. 3B is a perspective illustration of an embodiment of a proximal shaft of the FFR catheter of FIG. 1 with a guidewire received therein.

DETAILED DESCRIPTION OF THE INVENTION

Specific embodiments of the present invention are now described with reference to the figures, wherein like reference numbers indicate identical or functionally similar elements. The terms "distal" and "proximal", when used in the following description to refer to a catheter or delivery system are with respect to a position or direction relative to the treating clinician. Thus, "distal" and "distally" refer to positions distant from, or in a direction away from the treating clinician, and the terms "proximal" and "proximally" refer to positions near, or in a direction toward the clinician. The terms "distal" and "proximal", when used in the following description to refer to a vessel or lesion, are used with reference to the direction of blood flow. Thus, "distal" and "distally" refer to positions in a downstream direction with respect to the direction of blood flow and the terms "proximal" and "proximally" refer to positions in an upstream direction with respect to the direction of blood flow.

The following detailed description is merely exemplary in nature and is not intended to limit the invention or the application and uses of the invention. Although the description of the invention is in the context of treatment of blood vessels such as the coronary arteries, the invention may also be used in any other body passageways where it is deemed useful such as, but not limited to peripheral arteries, carotid arteries, renal arteries, and/or venous applications. Furthermore, there is no intention to be bound by any expressed or implied theory presented in the preceding technical field, background, brief summary or the following detailed description.

Figure 1:
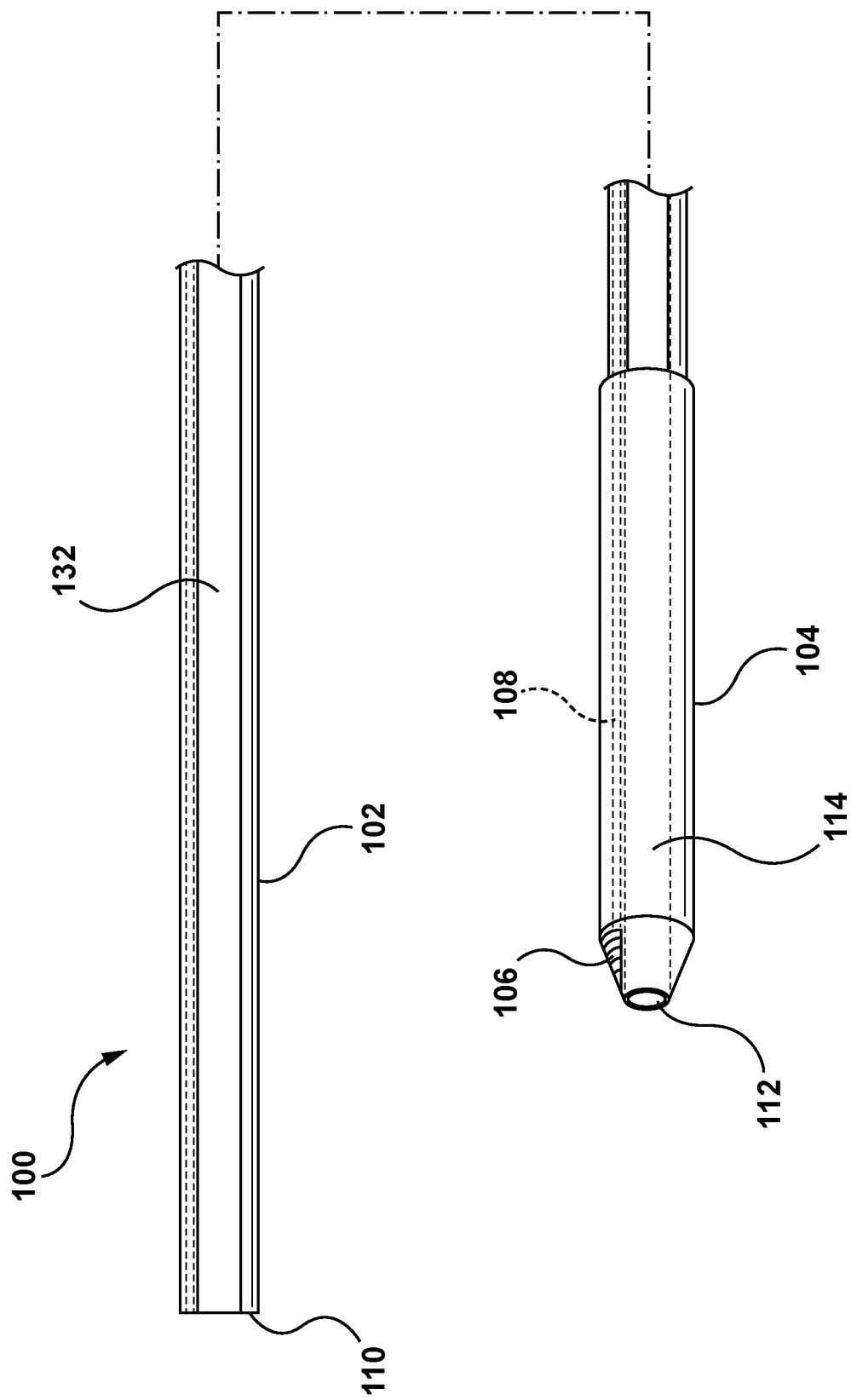
FIG. 1 is a side illustration of an FFR catheter in accordance with an embodiment hereof.

A catheter 100 (FFR catheter, or FFR micro-catheter) used for calculating a Fractional Flow Reserve (FFR) according to an embodiment of the present disclosure is shown in FIGS. 1-7. FFR catheter 100 includes a proximal shaft 102, a distal shaft 104, a pressure sensor 106, and at least one pressure sensor wire 108, as shown in FIG. 1. FFR catheter 100 further includes a proximal end 110 and a distal end 112. FFR catheter 100 is configured to receive a guidewire 800 therein, as explained in more detail below. FFR catheter 100 is configured with proximal shaft 102 coupled directly to distal shaft 104. However, this is not meant to be limiting, and other components may be disposed between proximal shaft 102 and distal shaft 104.

Figure 2:
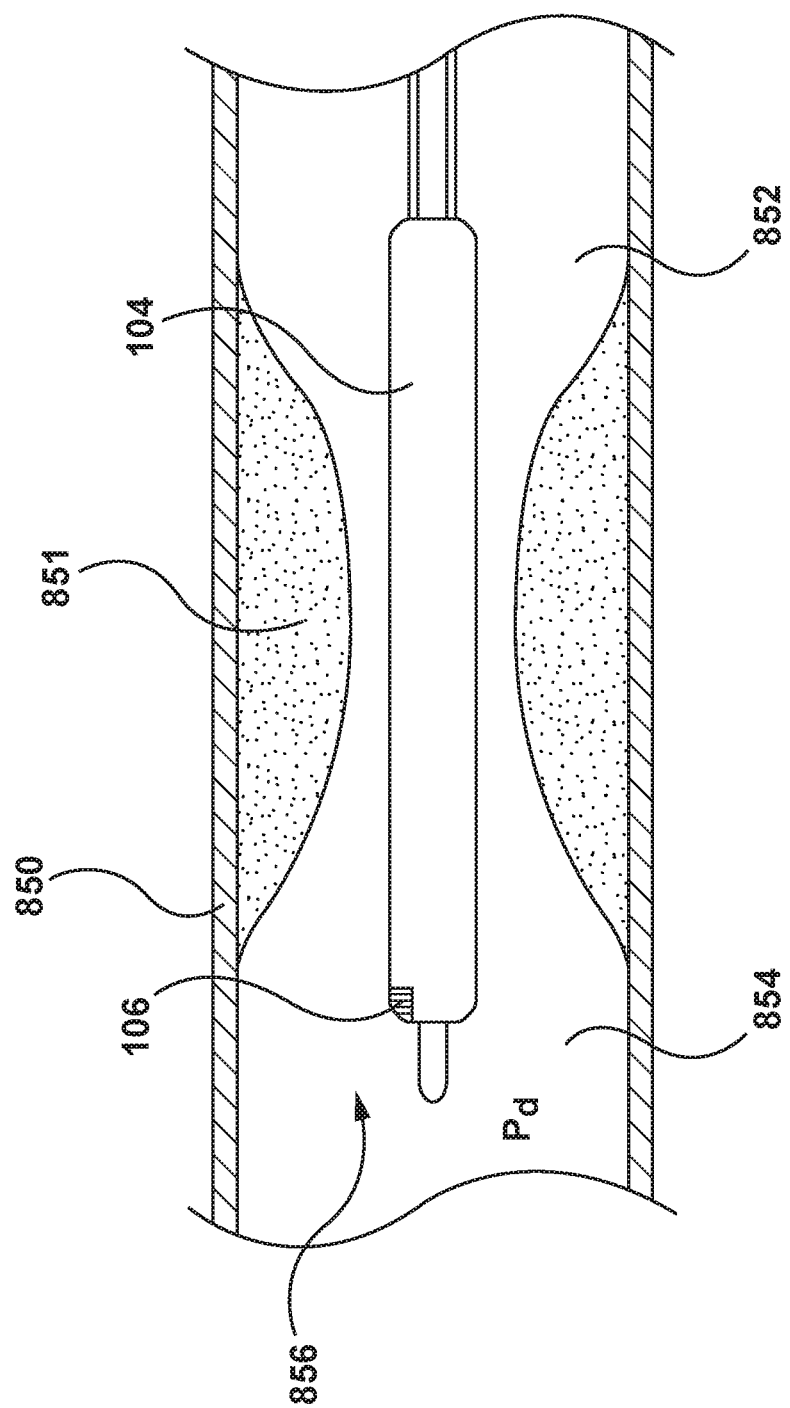
FIG. 2 is a side illustration of a distal end of the FFR catheter of FIG. 1 disposed at a treatment site of a lesion.

FFR catheter 100 is configured to be disposed with a proximal portion of proximal shaft 102 extending outside of a patient, and a distal portion of distal shaft 104 positioned in situ within a lumen 856 of a vessel 850 having a lesion 851, as shown in FIG. 2. In an embodiment, vessel 850 is a blood vessel such as, but not limited to a coronary artery. Lesion 851 is generally representative of any blockage or other structural arrangement that results in a restriction to the flow of fluid through lumen 856 of vessel 850. Lesion 851 may be a result of plaque buildup, including without limitation plaque components such as fibrous, fibro-lipidic (fibro fatty), necrotic core, calcified (dense calcium), blood, fresh thrombus, and mature thrombus. The composition of lesion 851 will generally depend on the type of vessel being evaluated. In that regard, it is understood that embodiments hereof are applicable to various types of blockages or other narrowing of a vessel that results in decreased fluid flow. FFR catheter 100 is configured to measure a distal pressure $P_d$ of vessel 850 on distal side 854 of lesion 851 when disposed therethrough, as shown in FIG. 2.

Figure 4A:
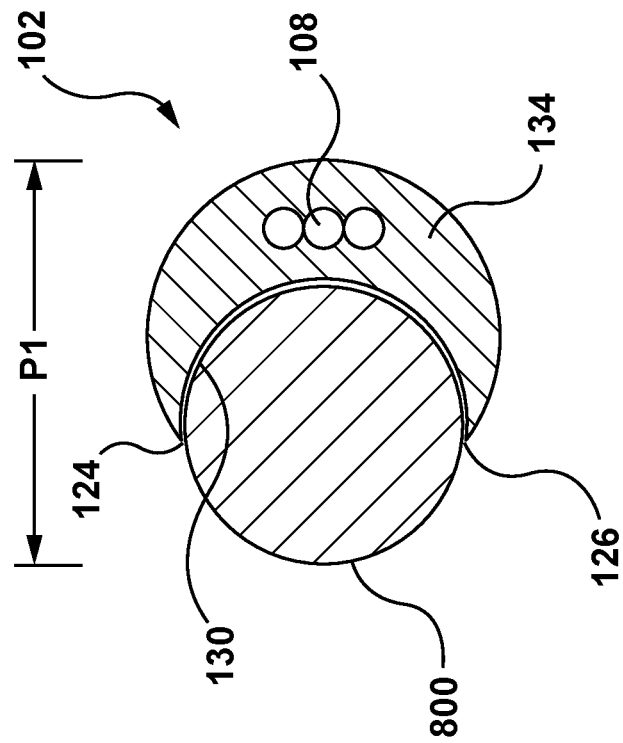
FIG. 4A is a cross-sectional illustration of the proximal shaft of FIG. 3A, taken along line 4A-4A.
Figure 4B:
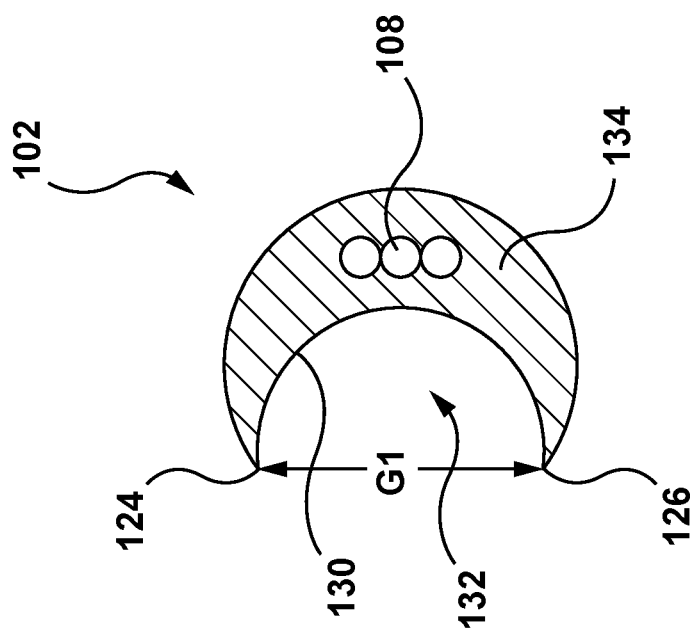
FIG. 4B is a cross-sectional illustration of the proximal shaft of FIG. 3B, taken along line 4B-4B.

Referring to FIGS. 3A-3B and 4A-4B, in an embodiment, proximal shaft 102 of FFR catheter 100 includes a proximal end 120 and a distal end 122. Proximal shaft 102 is substantially c-shaped in cross-section, as shown in FIGS. 3A and 4A. Thus, a cross-sectional profile of proximal shaft 102, shown in FIG. 4A, includes a first circumferential end 124, a second circumferential end 126, and a gap G1 between first circumferential end 124 and second circumferential end 126. An inner surface 130 of proximal shaft 102 extends from first circumferential end 124 to second circumferential end 126. Inner surface 130, first circumferential end 124, and second circumferential end 126, define a groove 132 configured to receive a guidewire therein. FIGS. 3B and 4B show proximal shaft 102 with a guidewire 800 disposed in groove 132. As illustrated in FIG. 4B, proximal shaft 102 includes a first cross-sectional profile P1 with guidewire 800 received in groove 132. Proximal shaft 102 further includes a proximal shaft wall 134 opposite groove 132. A proximal portion of pressure sensor wire 108 is disposed within proximal shaft wall 134. In an embodiment, proximal shaft 102 may be 100 to 150 cm long. Inner surface 130 of proximal shaft 102 may include a lubricious coating thereon. The lubricious coating on inner surface 130 of proximal shaft 102 may include, but is not limited to polytetrafluoroethylene (PTFE), or any other materials suitable for purposes of the present disclosure.

Figure 5:
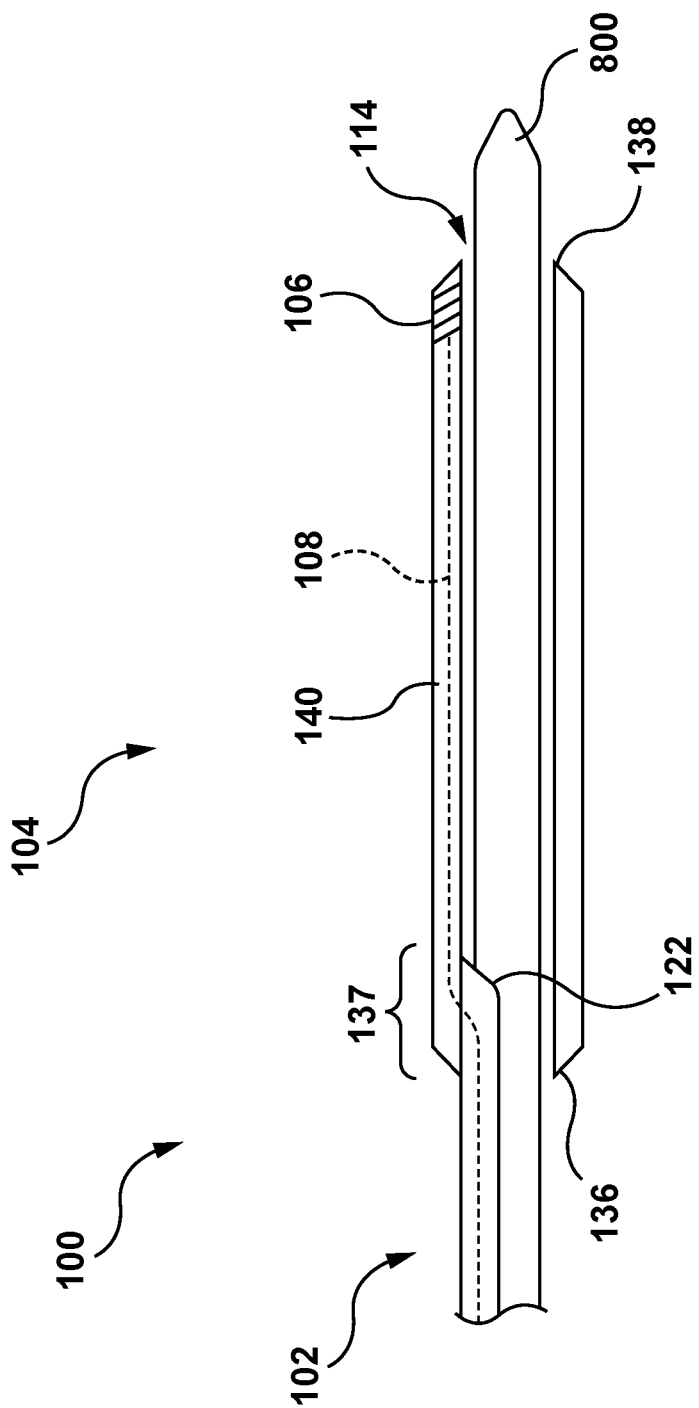
FIG. 5 is a cut-away side illustration of an embodiment of a distal shaft of the FFR catheter of FIG. 1 with a guidewire received therein.

FIG. 5 shows an embodiment of distal shaft 104 of FFR catheter 100. Distal shaft 104 includes a proximal end 136 and a distal end 138 defining a guidewire lumen 114 therethrough. Distal shaft 104 further includes pressure sensor 106 disposed on a distal portion of distal shaft 104. Pressure sensor 106 may be disposed on a distal tip (not shown) of FFR catheter 100, which is considered a distal portion of distal shaft 104. A distal portion of pressure sensor wire 108 is coupled to pressure sensor 106 and extends proximally in a distal shaft wall 140 of distal shaft 104. Proximal end 136 of distal shaft 104 is configured to accept distal end 122 of proximal shaft 102 therein at a transition region 137. Proximal shaft 102 and distal shaft 104 are coupled to each other in transition region 137. Thus, transition region 137 is where distal shaft 104 and proximal shaft 102 overlap, as shown in FIG. 5. Distal shaft 104 and proximal shaft 102 may be coupled to each other by, for example, and not by way of limitation, adhesives, fusing, welding, or any other method suitable for the purposes of the present disclosure. Distal shaft 104 is further configured to extend from a proximal side 852 of lesion 851, through lesion 851 to distal side 854 of lesion 850, such that pressure sensor 106 may be disposed on distal side 854 of lesion 851 as shown in FIG. 2. In an embodiment, distal shaft 104 may be 20 to 50 cm long.

While proximal shaft 102 and distal shaft 104 of FFR catheter 100 have been described separately, they are described in such a manner for convenience and FFR catheter 100 may be constructed unitarily such that proximal shaft 102 and distal shaft 104 are part of a unitary shaft.

FFR catheter 100 may be formed of a polymeric material, non-exhaustive examples of which include, but are not limited to polyethylene, PEBA, polyamide and/or combinations thereof, either blended or co-extruded. Optionally, FFR catheter 100, or some portion thereof, may be formed as a composite having a reinforcement material incorporated within a polymeric body in order to enhance strength and/or flexibility. Suitable reinforcement layers include braiding, wire mesh layers, embedded axial wires, embedded helical or circumferential wires, and the like.

Pressure sensor 106 of distal shaft 104, as shown in FIGS. 1, 2, 5, and 6 may be a piezo-resistive pressure sensor, a piezo-electric pressure sensor, a capacitive pressure sensor, an electromagnetic pressure sensor, an optical pressure sensor, a differential pressure sensor, and/or combinations thereof or other sensors suitable for the purpose described herein. Pressure sensor 106 is configured such that pressure sensor 106 measures distal pressure $P_d$ of a fluid outside distal shaft 104, as shown in FIG. 2. Pressure sensor 106 is further configured to communicate distal pressure $P_d$ with a processor 242 (FIG. 6) as described in greater detail below. Pressure sensor 106 is disposed in distal shaft wall 140 (FIG. 5) of distal shaft 104 such that pressure sensor 106 is disposed on distal side 854 of lesion 851 when distal shaft 104 is positioned therethrough, as shown in FIG. 2. Pressure sensor 106 is coupled to distal shaft 104 by, for example, and not by way of limitation, adhesives, fusing, welding, for any other method suitable for the purposes of the present disclosure. Further, additional features may be provided as part of distal shaft 104 for housing pressure sensor 106, such as pockets, openings, and similar features.

Figure 6:
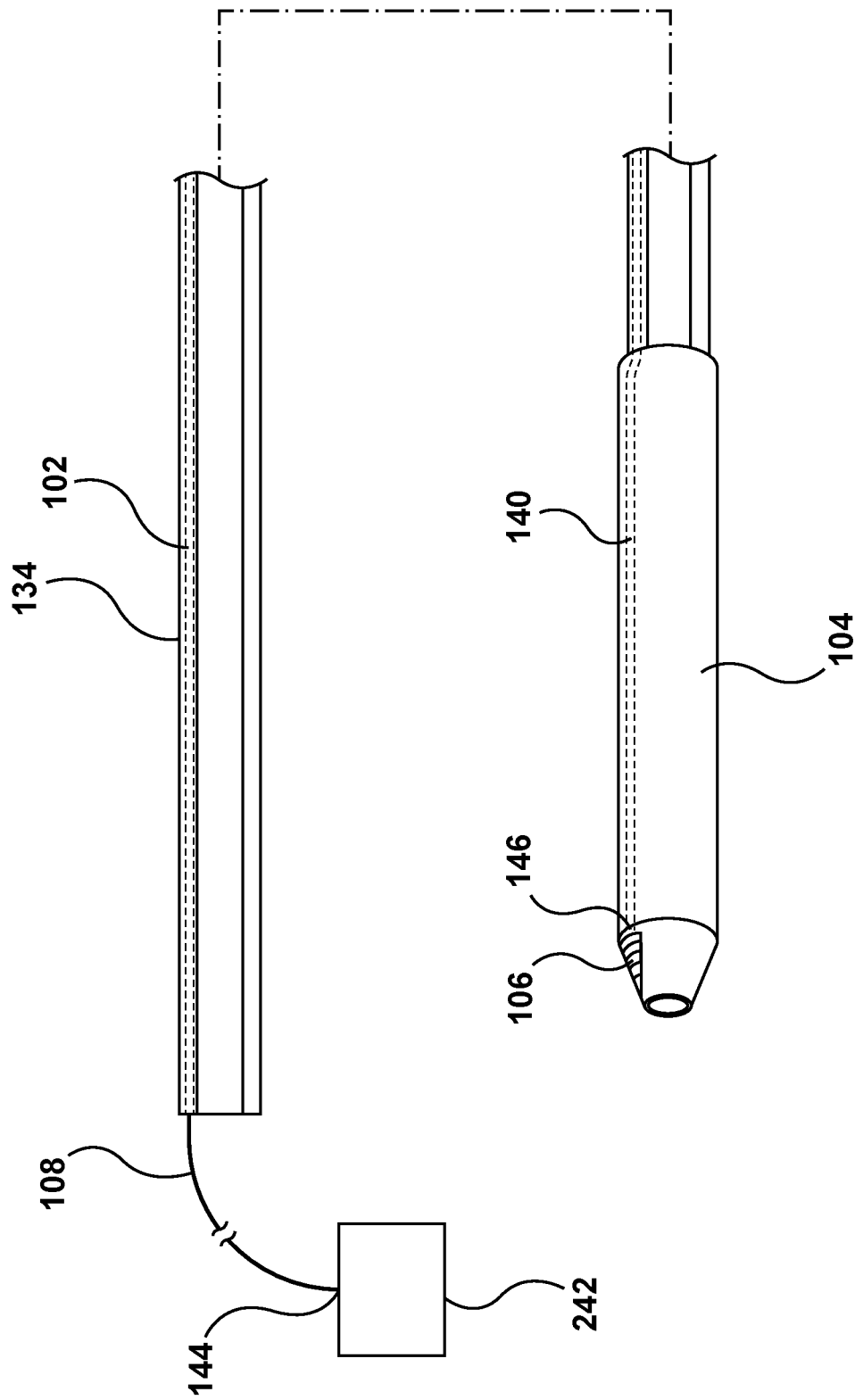
FIG. 6 is a side illustration of the FFR catheter of FIG. 1 coupled to a processor.

Referring to FIG. 6, pressure sensor wire 108 includes a proximal end 144 and a distal end 146. Proximal end 144 of pressure sensor wire 108 is operably coupled to processor 242 and distal end 146 of pressure sensor wire 108 is operably coupled to pressure sensor 106 such that pressure sensor 106 is in communication with processor 242. A proximal portion of pressure sensor wire 108 is disposed within proximal shaft wall 134 of proximal shaft 102 and a corresponding distal portion of pressure sensor wire 108 is disposed in distal shaft wall 140 of distal shaft 104. Pressure sensor wire 108 therefore extends proximally from pressure sensor 106, through distal shaft wall 140, transitioning into proximal shaft wall 134 in transition region 137, through corresponding proximal shaft wall 134, exiting through a proximal port 248 of FFR catheter 100 to processor 242. Pressure sensor wire 108 may be coupled to pressure sensor 106 by, for example, and not by way of limitation, adhesives, fusing, welding, or any other method suitable for the purposes of the present disclosure. Pressure sensor wire 108 may be coupled to processor 242 by, for example, and not by way of limitation, cables, connectors, antennas, routers, switches, or any other method suitable for the purposes of the present disclosure.

While FIGS. 1-4 show three (3) pressure sensor wires 108 and FIGS. 5-6 show one (1) pressure sensor wire 108, this is not meant to limit the design, and more or fewer pressure sensor wires 108 may be utilized. Moreover, pressure sensor wire(s) 108 may be eliminated in embodiments wherein a signal from pressure sensor 106 is sent to processor 242 other than via pressure sensor wire 108, such as, but not limited to, wireless transmission.

Processor 242 may be any processor suitable for the purposes described herein. Processor 242 may include such components as a CPU, a display device, an amplification and filtering device, an analog-to-digital converter, and various other components. Processor 242 is configured to receive a proximal pressure measurement $P_a$ and a distal pressure measurement $P_d$. Processor 242 is further configured to provide a continuous display of calculated Fractional Flow Reserve (FFR). Processor 242 is coupled to pressure sensor wire 108 such that processor 242 is in communication with pressure sensor 106 as described previously. Processor 242 may be coupled to proximal end 144 of pressure sensor wire 108 via various communication pathways, including but not limited to one or more physical connections including electrical, optical, and/or fluid connections, a wireless connection, and/or combinations thereof. Accordingly, it is understood that additional components (e.g., cables, connectors, antennas, routers, switches, etc.) not illustrated in FIGS. 4-7 may include devices to facilitate communication between proximal end 144 of pressure sensor wire 108 and processor 242. In other embodiments, instead of pressure sensor wire 108, communication between pressure sensor 106 and processor 242 may be accomplished wirelessly.

Figure 7:
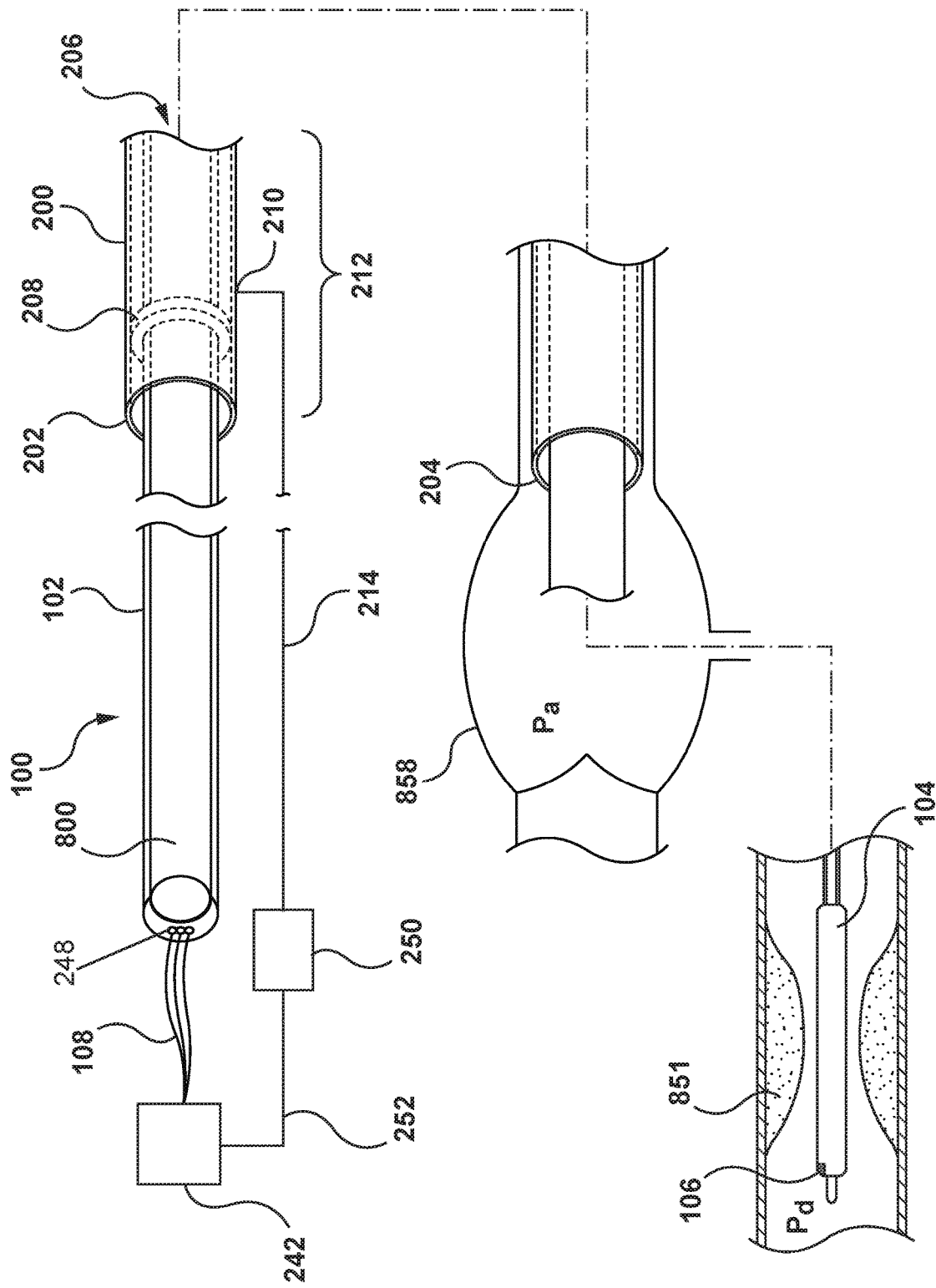
FIG. 7 is a perspective illustration of a FFR system including the FFR catheter of FIG. 1 disposed through a guide catheter with a distal end disposed in an aorta and the FFR catheter extending distally of the guide catheter to a treatment site of a lesion.

Referring to the embodiment illustrated in FIG. 7, a guide catheter 200 includes a proximal end 202 and a distal end 204. The guide catheter 200 defines a lumen 206. Lumen 206 is sized to receive FFR catheter 100 therethrough. Guide catheter 200 further includes a seal 208 at a proximal portion 212 of guide catheter 200, as described in greater detail below. Guide catheter 200 is used as a guide to such that FFR catheter 100 is advanced therethrough to the desired treatment site. Guide catheter 200 is further configured to fluidly communicate a proximal, or aortic (AO) pressure $P_a$ to an external pressure transducer 250. Guide catheter 200 is configured to be disposed with a proximal portion thereof extending outside of a patient and a distal portion thereof positioned in situ within an aorta, such as at an aortic sinus 858.

Seal 208 may be of a substantially annular shape. Seal 208 is configured such that fluid within lumen 206 of guide catheter 200 does not exit out proximal end 202 of guide catheter 200. Seal 208 is disposed within lumen 206 at proximal portion 212 of guide catheter 200 such that an outer circumferential surface of seal 208 mates with an inner circumferential surface of guide catheter 200. Seal 208 is further configured such that an inner circumferential surface of seal 208 mates with an outer surface of proximal shaft 102 and guidewire 800, received therein. More specifically, the substantially circular/oblong outer surface profile of proximal shaft 102 with guidewire 800 received therein mates with the corresponding substantially circular/oblong inner surface shape of seal 208 forming a fluid-tight seal. The substantially circular/oblong shape of the proximal shaft 102 and the guidewire 800 received therein optimizes sealing at the proximal end of guide catheter 200. Moreover, the substantially simple circular/oblong profile may make seal 208 easier to fit, more effective to seal, and less expensive to manufacture than current, more complex-shaped seals.

With an understanding of the components of FFR catheter 100 and guide catheter 200 above, it is now possible to describe the interactions of the various components to calculate a Fractional Flow Reserve (FFR).

Referring to FIG. 7, guide catheter 200 and guidewire 800 are advanced through the vasculature to a desired site. Guidewire 800 may be back-loaded into FFR catheter 100 (i.e., the proximal end of guidewire 800 is loaded into the distal end of guidewire lumen 114 at distal end 138 of distal shaft 104). FFR catheter 100 may then be advanced over guidewire 800 and through lumen 206 of guide catheter 200 to the desired treatment site. In particular, with distal end 204 of guide catheter 200 disposed at a desired site proximal of lesion 851, such as in the sinus 858, distal shaft 104 of FFR catheter 100 is advanced through lumen 206 and distal of distal end 204 of guide catheter 200. FFR catheter 100 is advanced such that distal shaft 104 is disposed through lesion 851 of vessel 850. Blood flow from aortic sinus 858 fills lumen 206 and tubing 214 via a port 210 of proximal portion 212 of guide catheter 200. The blood pressure $P_a$ at distal end 204 of guide catheter 200 is measured by external pressure transducer 250 via the fluid (blood) column extending through lumen 206 and tubing 214. Thus, external pressure transducer 250 is configured to measure proximal, or aortic (AO) pressure $P_a$ at distal end 204 of guide catheter 200.

External pressure transducer 250 is configured to communicate measured proximal pressure $P_a$ to processor 242 via pressure transducer wire 252, as shown in FIG. 7. While pressure transducer 250 is shown in FIG. 7 as communicating measured proximal pressure $P_a$ with processor 242 via pressure transducer wire 252, this is not meant to limit the design and pressure transducer 250 may communicate with processor 242 by any means suitable for the purposes described, including, but not limited to, electrical cables, optical cables, or wireless devices. Simultaneously, pressure sensor 106 measures distal pressure $P_d$ distal of lesion 851. Distal pressure $P_d$ is communicated to processor 242, as explained above. Processor 242 calculates the Fractional Flow Reserve (FFR) based on the distal pressure $P_a$ divided by the proximal/aortic pressure $P_a$, or FFR=$P_d/P_a$.

As explained above, FFR catheter 100 with guidewire 800 received in groove 132 of proximal shaft 102 has a first cross-sectional profile P1 (FIG. 4B). The first cross-sectional profile P1 is a reduced profile as compared to a tubular proximal shaft with a guidewire disposed outside of the proximal shaft. As further explained above, because the proximal or aortic pressure $P_a$ is measured using the fluid column within lumen 206 of guide catheter 200 between an outer surface of a guidewire/FFR proximal shaft combination and an inner surface of the guide catheter, a larger profile may lead to errors in the measured proximal or aortic pressure $P_a$. Such errors are carried through to the FFR calculation noted above because the measured proximal pressure $P_a$ is used in the FFR calculation. Thus, reducing the cross-sectional profile P1 leads to a smaller potential for error in the proximal pressure $P_a$, and hence a smaller potential for error in the FFR calculation.

Since guidewire 800 remains constant, the smaller the cross-sectional profile P1 of proximal shaft 102, the smaller the error in proximal (AO) pressure measurement $P_a$. Stated another way, the smaller the cross-sectional profile P1 of proximal shaft 102 of FFR catheter 100, the more accurate the proximal (AO) pressure measurement $P_a$.

Figure 8:
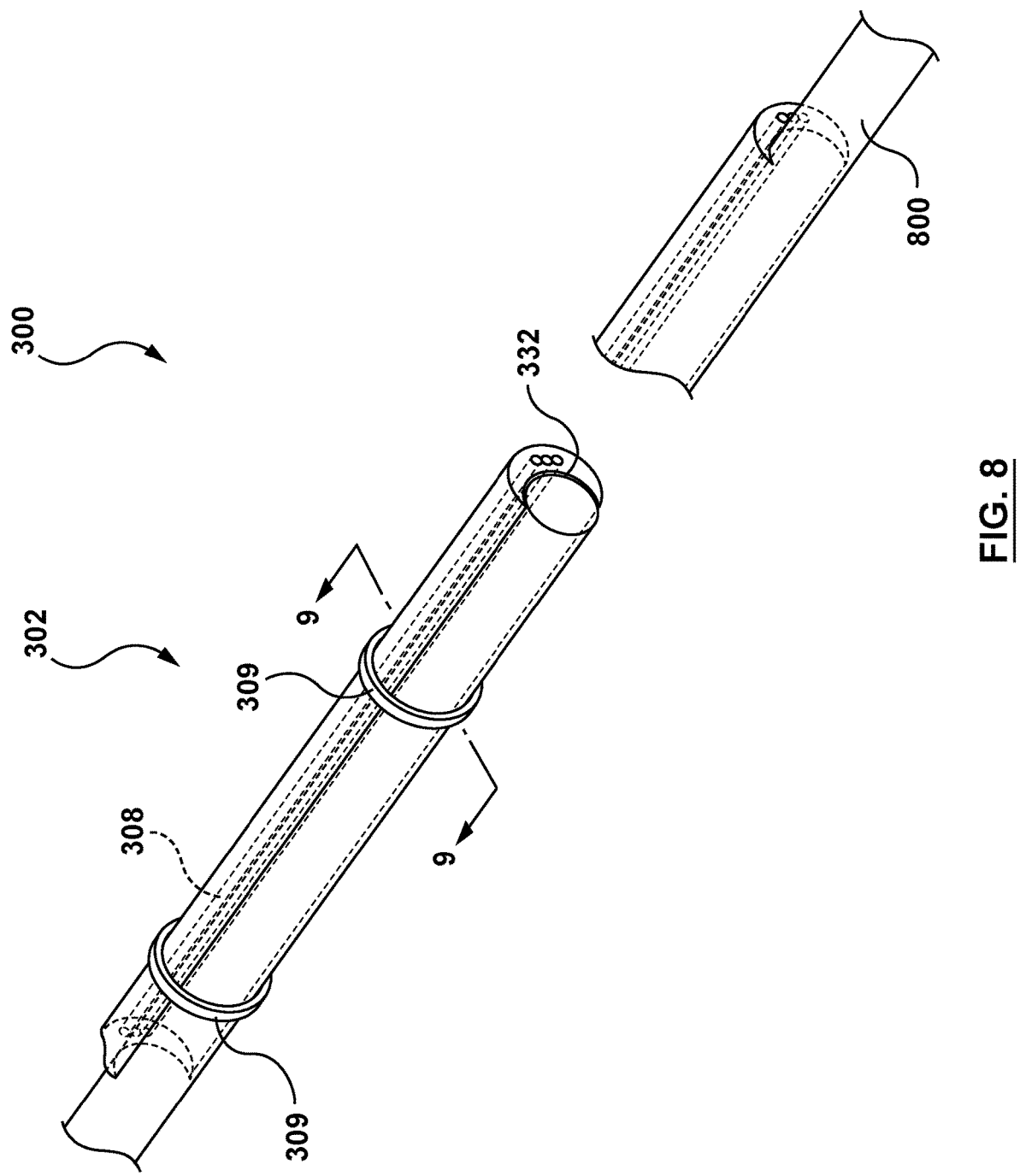
FIG. 8 is a perspective illustration of another embodiment of a proximal shaft of an FFR catheter with a guidewire received therein.
Figure 9:
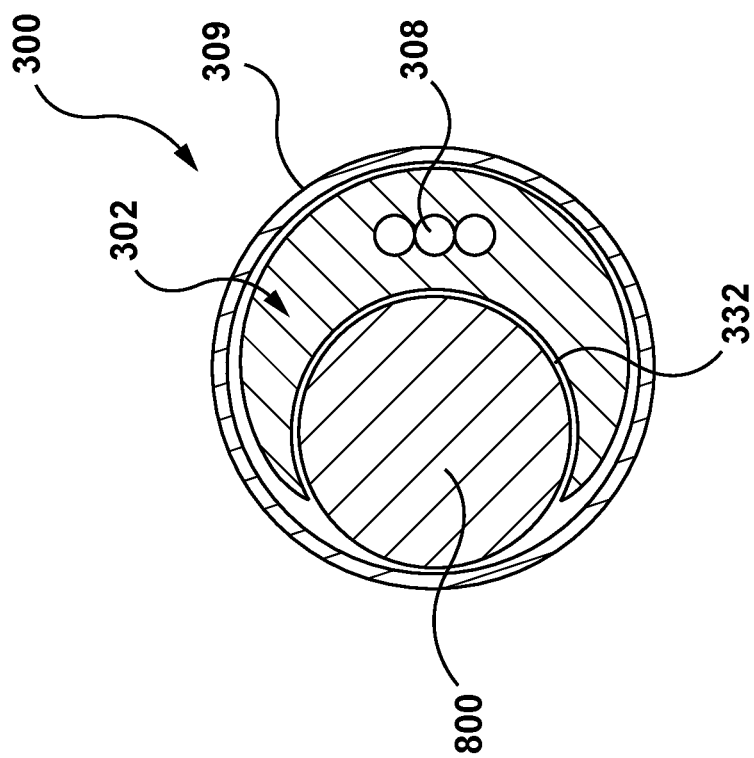
FIG. 9 is a cross-sectional illustration of the proximal shaft of FIG. 8, taken along line 9-9.

FIGS. 8-9 illustrate another embodiment of an FFR catheter 300 of the present disclosure. FFR catheter 300 of FIGS. 8-9 is similar to FFR catheter 100 of FIGS. 1-7, except proximal shaft 302 of FFR catheter 300 further includes a plurality of bands 309, as shown in FIG. 8. Accordingly, FFR catheter 300 includes the proximal shaft 302, a distal shaft (not shown), a pressure sensor (not shown), and a pressure sensor wire(s) 308. Bands 309 are of a generally tubular configuration. Bands 309 are configured to extend circumferentially around an outer surface of proximal shaft 302 and an outer surface of guidewire 800 received therein. Bands 309 are disposed circumferentially about an outer surface of proximal shaft 302 and an outer surface of guidewire 800 such that bands 309 retain guidewire 800 within a groove 332 of proximal shaft 302, as shown in FIG. 9. Stated another way, guidewire 800 is slidably received groove 332 of proximal shaft 302 and retained therein by bands 309. Although FFR catheter 300 of FIGS. 8-9 is shown with two (2) bands 309, this is not meant to limit the design and more or fewer bands 309 may be utilized. Bands 309 of FFR catheter 300 may be formed, for example, and not by way of limitation, of woven polyester such as polyethylene terephthalate, polytetrafluoroethylene (PTFE), or any other materials suitable for purposes of the present disclosure. Bands 309 may be coupled to proximal shaft 302 in a manner such as, but not limited to adhesives, sutures, friction, or other methods suitable for the purposes of the present disclosure. Further, although FIG. 9 shows bands 309 as circular, bands 309 may be flexible such that bands 309 fit the shape of guidewire 800. In other words bands 309 may be contoured to fit the shape of proximal shaft 302 with guidewire 800 disposed therein.

Figure 10:
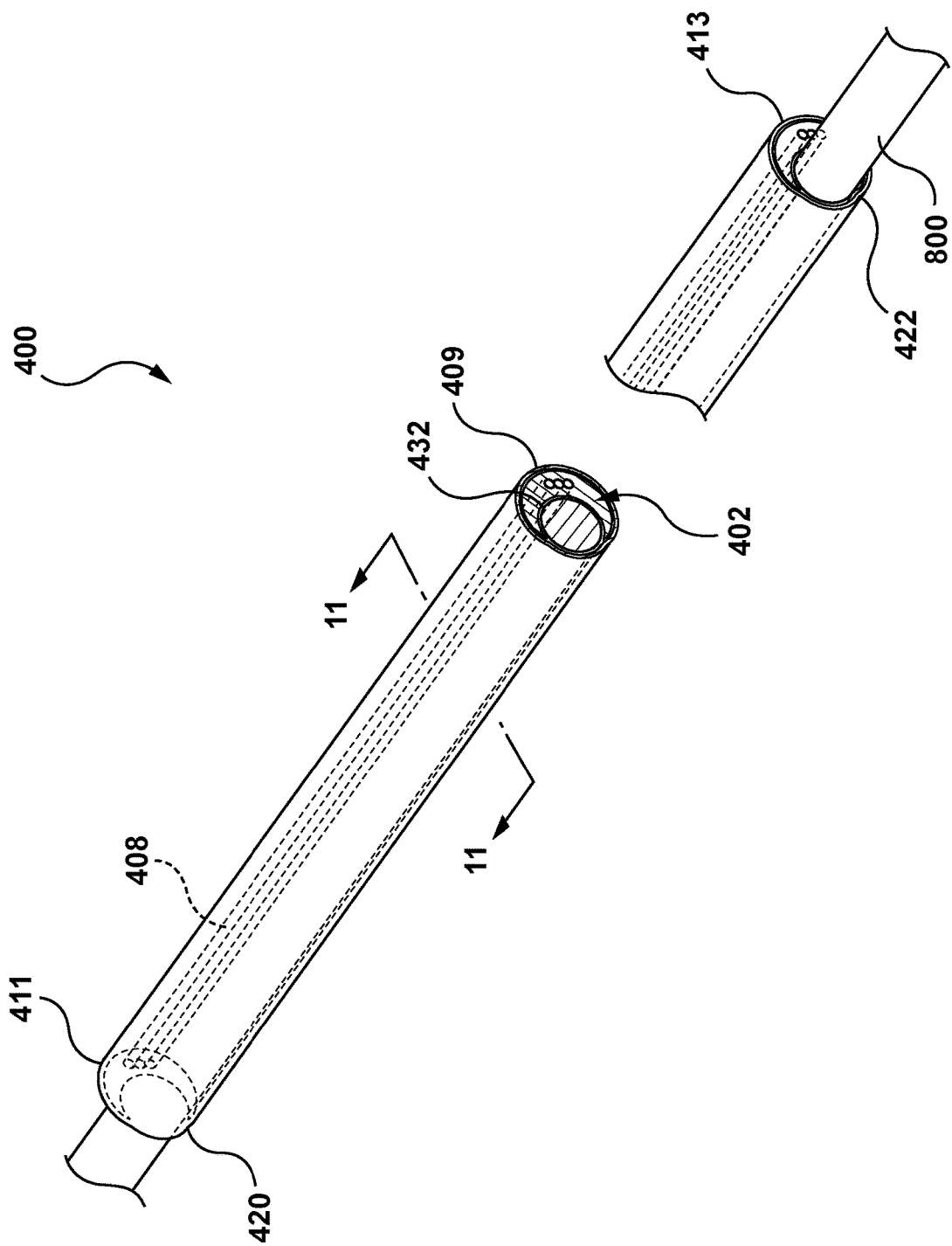
FIG. 10 is a perspective illustration of another embodiment of a proximal shaft of an FFR catheter with a guidewire received therein.
Figure 11:
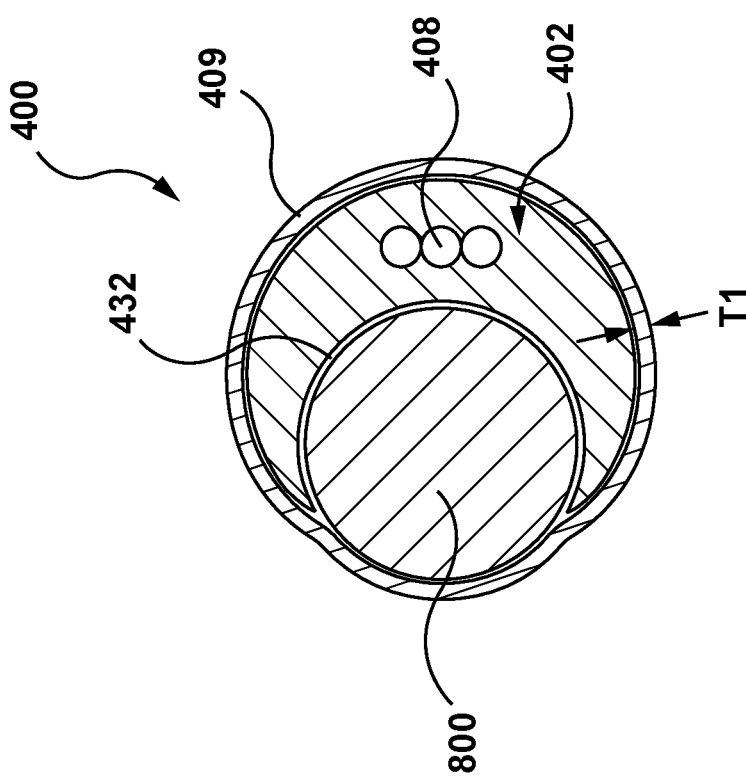
FIG. 11 is a cross-sectional illustration of the proximal shaft of FIG. 10, taken along line 11-11.

FIGS. 10-11 illustrate another embodiment of an FFR catheter 400 of the present disclosure. FFR catheter 400 is similar to FFR catheter 100 described above. Therefore, all of the details and alternatives of FFR catheter 400 will not be repeated. For example, FFR catheter 400 includes a distal shaft that is not shown. The distal shaft of FFR catheter 400 may be the same as distal shaft 104 of FFR catheter 100. Thus, FFR catheter 400 generally includes a proximal shaft 402, the distal shaft (not shown) with a pressure sensor (not shown), and at least one pressure sensor wire 408. In the embodiment of FIGS. 10-11, proximal shaft 402 of FFR catheter 400 further includes a sheath or cover 409. Cover 409 is of a generally tubular configuration, as shown in FIGS. 10-11. Cover 409 includes a proximal end 411 and a distal end 413, and is disposed around an outer surface of the proximal shaft 402. Cover 409 is configured to extend circumferentially around an outer surface of proximal shaft 402 and an outer surface of guidewire 800 received in a groove 432 of proximal shaft 402, as shown in FIG. 10. Cover 409 is disposed circumferentially about an outer surface of proximal shaft 402 and an outer surface of guidewire 800 such that cover 409 retains guidewire 800 within groove 432 of proximal shaft 402, as shown in FIG. 11. Stated another way, guidewire 800 is slidably received within groove 432 of proximal shaft 402 and retained therein by cover 409. Although cover 409 is shown in FIG. 10 as extending from a proximal end 420 to a distal end 422 of proximal shaft 402, this is not meant to limit the design, and cover 409 may extend over only a portion of proximal shaft 402. Moreover, cover 409 is shown in FIG. 11 with a uniform first wall thickness T1, but this is not meant to limit the design, and first wall thickness T1 may be non-uniform. Cover 409 of FFR catheter 400 may be formed, for example, and not by way of limitation, of polymers, such as, but not limited to woven polyesters such as polyethylene terephthalate, polytetrafluoroethylene (PTFE), or any other materials suitable for purposes of the present disclosure. Cover 409 may be coupled to proximal shaft 402 in a manner such as, but not limited to, adhesives, compression fit, or other methods suitable for the purposes of the present disclosure. As shown in FIG. 11, cover 409 may be contoured to fit the shaft of proximal shaft 402 with guidewire 800 disposed therein. This contoured shape may be provided by cover 409 being flexible and undersized such that guidewire 800 stretches cover 409.

Figure 12:
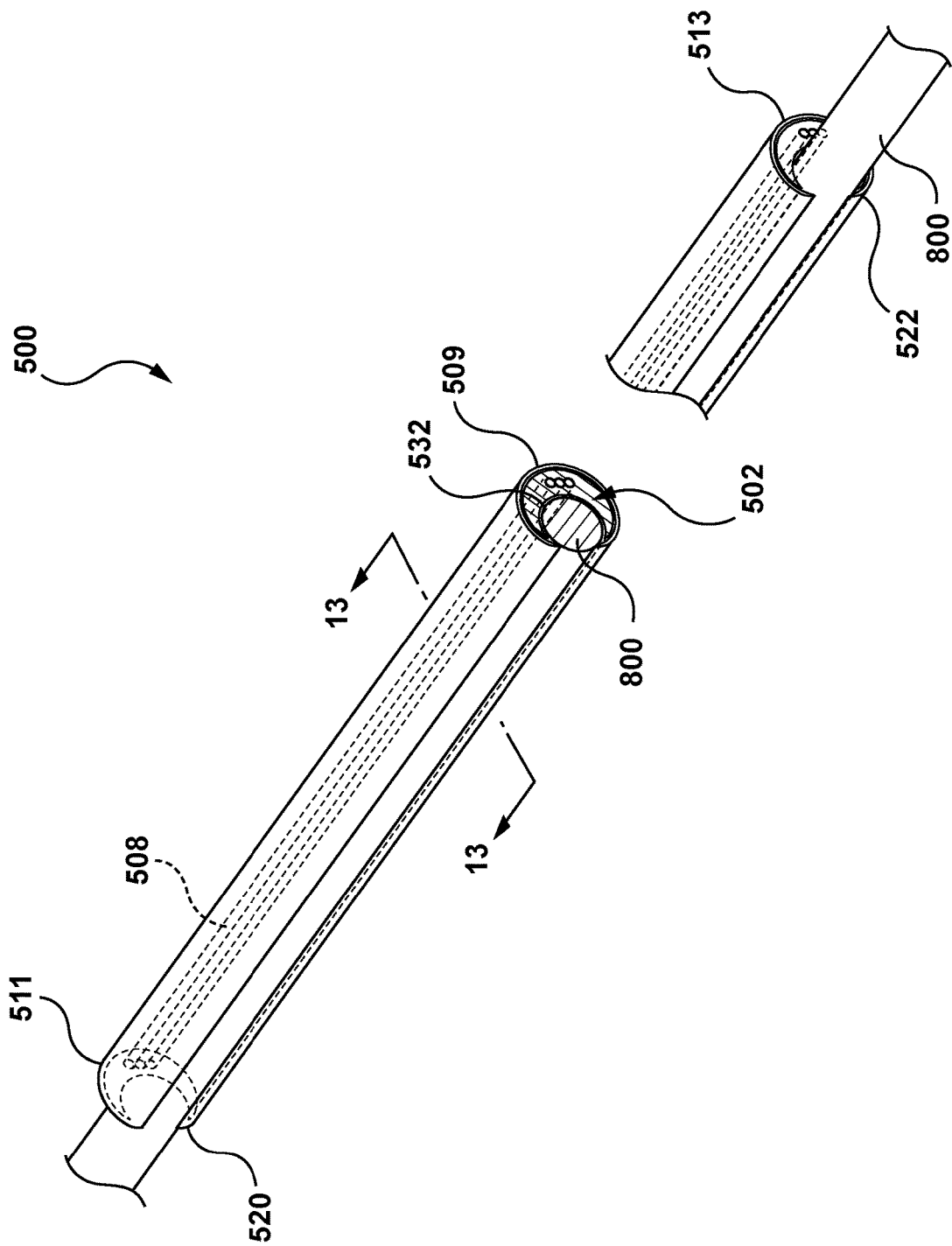
FIG. 12 is a perspective illustration of another embodiment of a proximal shaft of an FFR catheter with a guidewire received therein.
Figure 13:
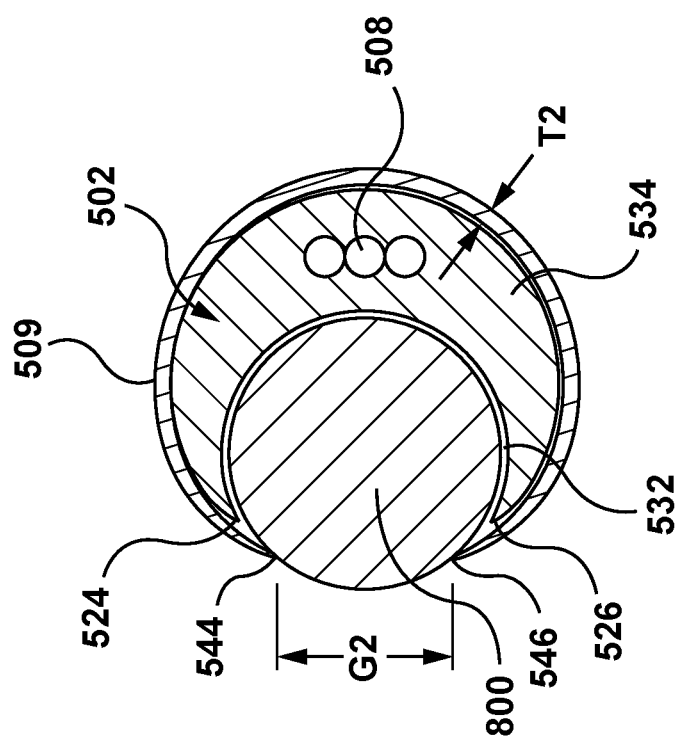
FIG. 13 is a cross-sectional illustration of the proximal shaft of FIG. 12, taken along line 13-13.

FIGS. 12-13 illustrate another embodiment of an FFR catheter 500 of the present disclosure. FFR catheter 500 is similar to FFR catheter 100 described previously. Therefore, all of the details and alternatives of FFR catheter 500 will not be repeated. For example, FFR catheter 500 includes a distal shaft that is not shown. The distal shaft of FFR catheter 500 may be the same as distal shaft 104 of FFR catheter 100. Thus, FFR catheter 500 generally includes a proximal shaft 502, the distal shaft (not shown) with a pressure sensor (not shown), and at least one pressure sensor wire 408. FFR catheter 500 further includes a cover 509 coupled to proximal shaft 502.

Cover 509 is a substantially c-shaped configuration, as shown in FIGS. 12-13. The c-shape of cover 509 is in the same direction as proximal shaft 502, as shown in FIG. 13. Cover 509 includes a longitudinal proximal end 511 and a longitudinal distal end 513, as shown in FIG. 12. Cover 509 further includes a first circumferential end 544, a second circumferential end 546, and a gap G2 between first circumferential end 554 and second circumferential end 546, as shown in FIG. 13, taken along line 13-13 of FIG. 12. Cover 509 is configured to extend circumferentially around an outer surface of a proximal shaft wall 534 of proximal shaft 502 and a portion of an outer surface of guidewire 800 received in a groove 532 of proximal shaft 502. More specifically, cover 509 is disposed circumferentially about the outer surface of proximal shaft wall 534 such that first circumferential end 544 and second circumferential end 546 extend beyond a first circumferential end 524 and a second circumferential end 526 of proximal shaft 502, respectively. Thus, with guidewire 800 disposed in groove 532 of proximal shaft 502, first circumferential end 544 and second circumferential end 546 extend partially around an outer surface of guidewire 800, thereby retaining guidewire 800 within groove 532 of proximal shaft 502. Stated another way, guidewire 800 is slidably received within groove 532 of proximal shaft 502 and retained therein by cover 509 partially surrounding guidewire 800. Although cover 509 is shown in FIG. 12 as extending from a proximal end 520 to a distal end 522 of proximal shaft 502, but this is not meant to limit the design, and cover 509 may extend over only a portion of proximal shaft 502. Moreover, cover 509 is shown in FIG. 13 with a uniform wall thickness T2, but this is not meant to limit the design, and wall thickness T2 may be non-uniform. Cover 509 of FFR catheter 500 may be formed, for example, and not by way of limitation, of polymers such as, but not limited to, woven polyesters such as polyethylene terephthalate, polytetrafluoroethylene (PTFE), or any other materials suitable for purposes of the present disclosure. Cover 509 may be coupled to proximal shaft 502 using adhesives, sutures, of other methods suitable for the purposes of the present disclosure.

Figure 14:
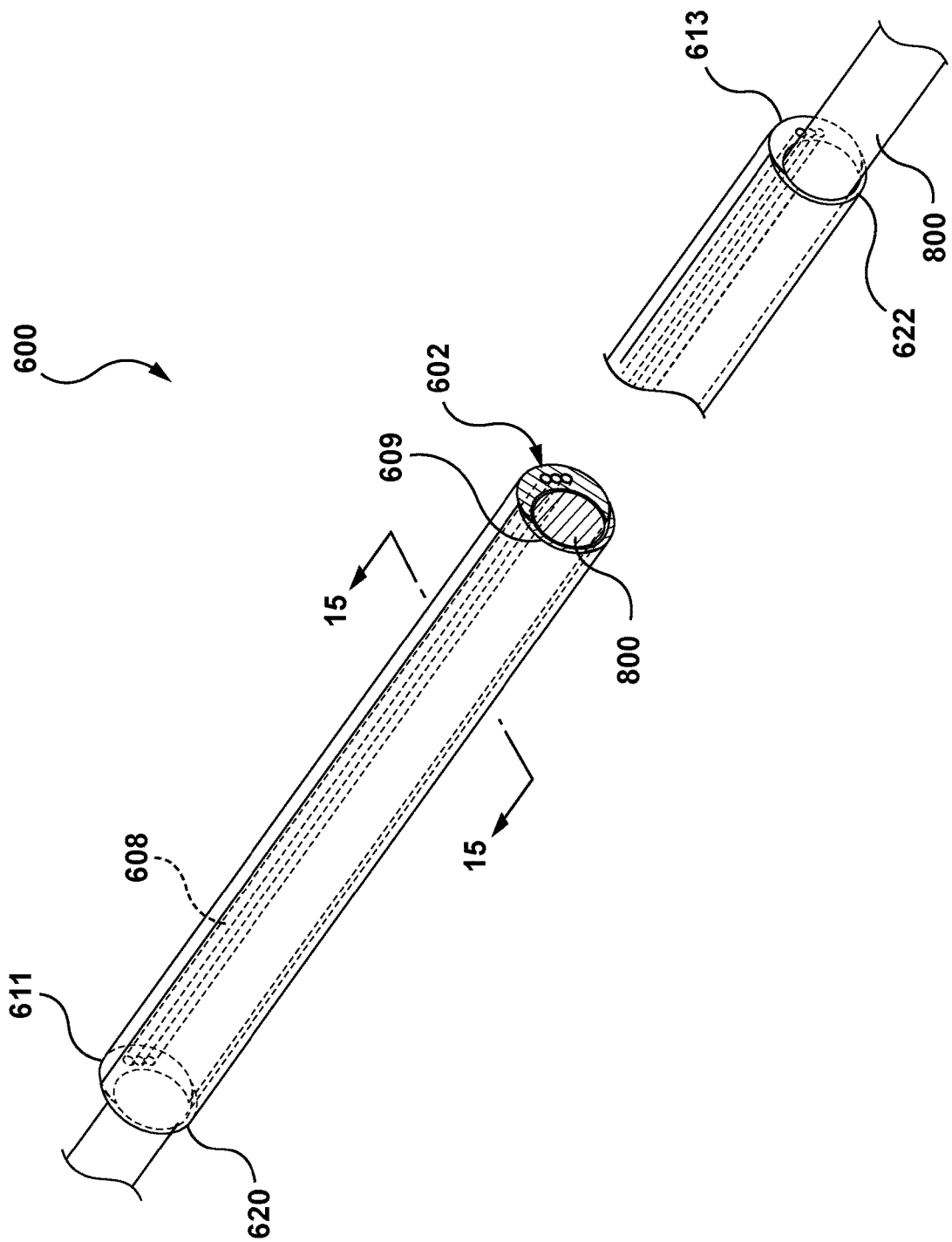
FIG. 14 is a perspective illustration of another embodiment of a proximal shaft of an FFR catheter with a guidewire received therein.
Figure 15:
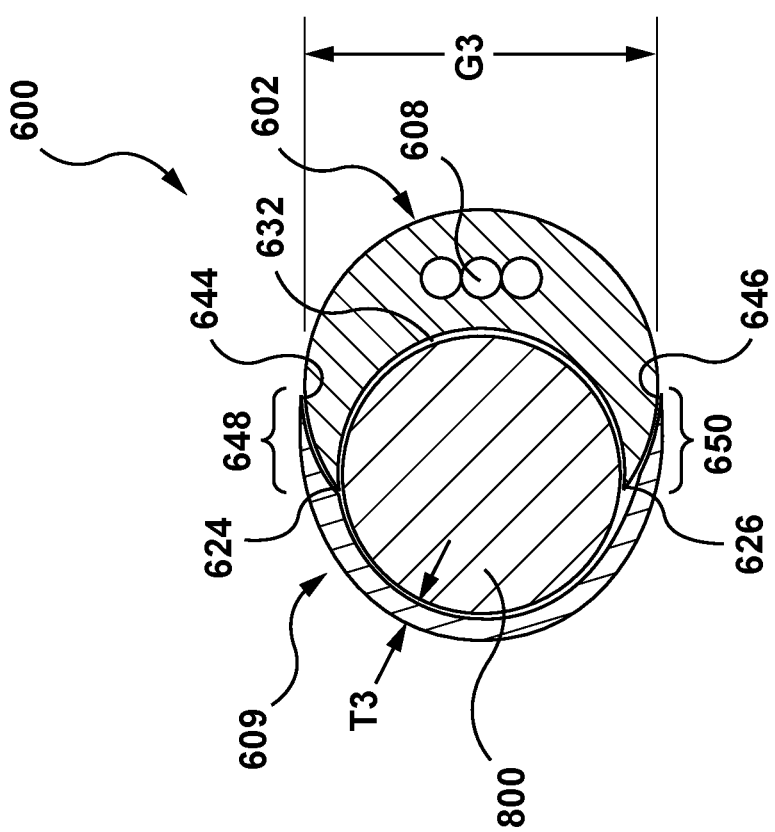
FIG. 15 is a cross-sectional illustration of the proximal shaft of FIG. 14, taken along line 15-15.

FIGS. 14-15 illustrate another embodiment of an FFR catheter 600 of the present disclosure. FFR catheter 600 is similar to FFR catheter 100 described previously. Therefore, all of the details and alternatives of FFR catheter 600 will not be repeated. For example, FFR catheter 600 includes a distal shaft that is not shown. The distal shaft of FFR catheter 600 may be the same as distal shaft 104 of FFR catheter 100. Thus, FFR catheter 600 generally includes a proximal shaft 602, the distal shaft (not shown) with a pressure sensor (not shown), and at least one pressure sensor wire 608. FFR catheter 600 further includes a cover 609 coupled to proximal shaft 602.

Cover 609 is substantially c-shaped in cross-section and faces the opposite direction of the substantially c-shaped cross-section of proximal shaft 602, as shown in FIGS. 14-15. Cover 609 includes a longitudinal proximal end 611 and a longitudinal distal end 613, as shown in FIG. 14. Cover 609 further includes a first circumferential end 644, a second circumferential end 646, and a gap G3 between first circumferential end 644 and second circumferential end 646, as shown in FIG. 15, taken along line 15-15 of FIG. 14. First circumferential end 644 of cover 609 overlaps with a first circumferential end 624 of proximal shaft 602 at a joint 648, and second circumferential end 646 of cover 609 overlaps with a second circumferential end of proximal shaft 602 at a joint 650, as shown in FIG. 15. Cover 609 is configured to extend circumferentially around an outer surface of guidewire 800 received in a groove 632 of proximal shaft 602. Stated another way, guidewire 800 is slidably received within groove 632 of proximal shaft 602 and is retained therein by cover 609. Although cover 609 is shown in FIG. 14 as extending from a proximal end 620 to a distal end 622 of proximal shaft 602, this is not meant to limit the design, and cover 609 may extend longitudinally along only a portion of proximal shaft 602. Further, there may be multiple shorter length covers 609 extending only a portion of the length of proximal shaft 602, such that multiple covers 609 are similar to bands 309 of FIGS. 8-9, except that bands that are similar to cover 609 do not extend around the entire outer surface of the proximal shaft 602. Moreover, cover 609 is shown in FIG. 15 with a uniform wall thickness T3, but this is not meant to limit the design, and wall thickness T3 may be non-uniform. Cover 609 of FFR catheter 600 may be formed, for example, and not by way of limitation, of polymers such as, but not limited to, woven polyesters such as polyethylene terephthalate, polytetrafluoroethylene (PTFE), or any other materials suitable for purposes of the present disclosure. Cover 609 may be coupled to proximal shaft 602 at joints 648, 650 using adhesives, sutures, of other methods suitable for the purposes of the present disclosure.

In the embodiments described above with respect to FIGS. 10-11, 12-13, and 14-15, covers 409, 509, and 609 are of thinner and more flexible material than the material of proximal shaft 402, 502, and 602. Thus, by utilizing covers 409, 509, or 609, the circumferential length of proximal shafts 402, 502, 602 to create grooves 432, 532, 632 may be reduced as compared to shaft 102, for example. Therefore, the overall profile of the proximal portion of FFR catheters 400, 500, 600 may be further reduced while securely maintaining the guidewire 800 in the respective groove 432, 532, 632.

FIGS. 16-19 illustrate another embodiment of an FFR catheter 700 of the present disclosure. FFR catheter 700 is similar to FFR catheter 100 described previously. Therefore, all of the details and alternatives of FFR catheter 700 will not be repeated. For example, FFR catheter 700 includes a distal shaft that is not shown. The distal shaft of FFR catheter 700 may be that same as distal shaft 104 of FFR catheter 100. Thus, FFR catheter 700 generally includes a proximal shaft 702, the distal shaft (not shown) with a pressure sensor (not shown), and at least one pressure sensor wire 708. Proximal shaft 702 of FFR catheter 700 further includes a collapsed configuration, a transitional configuration, and an expanded configuration, as explained in more detail below.

Figure 16:
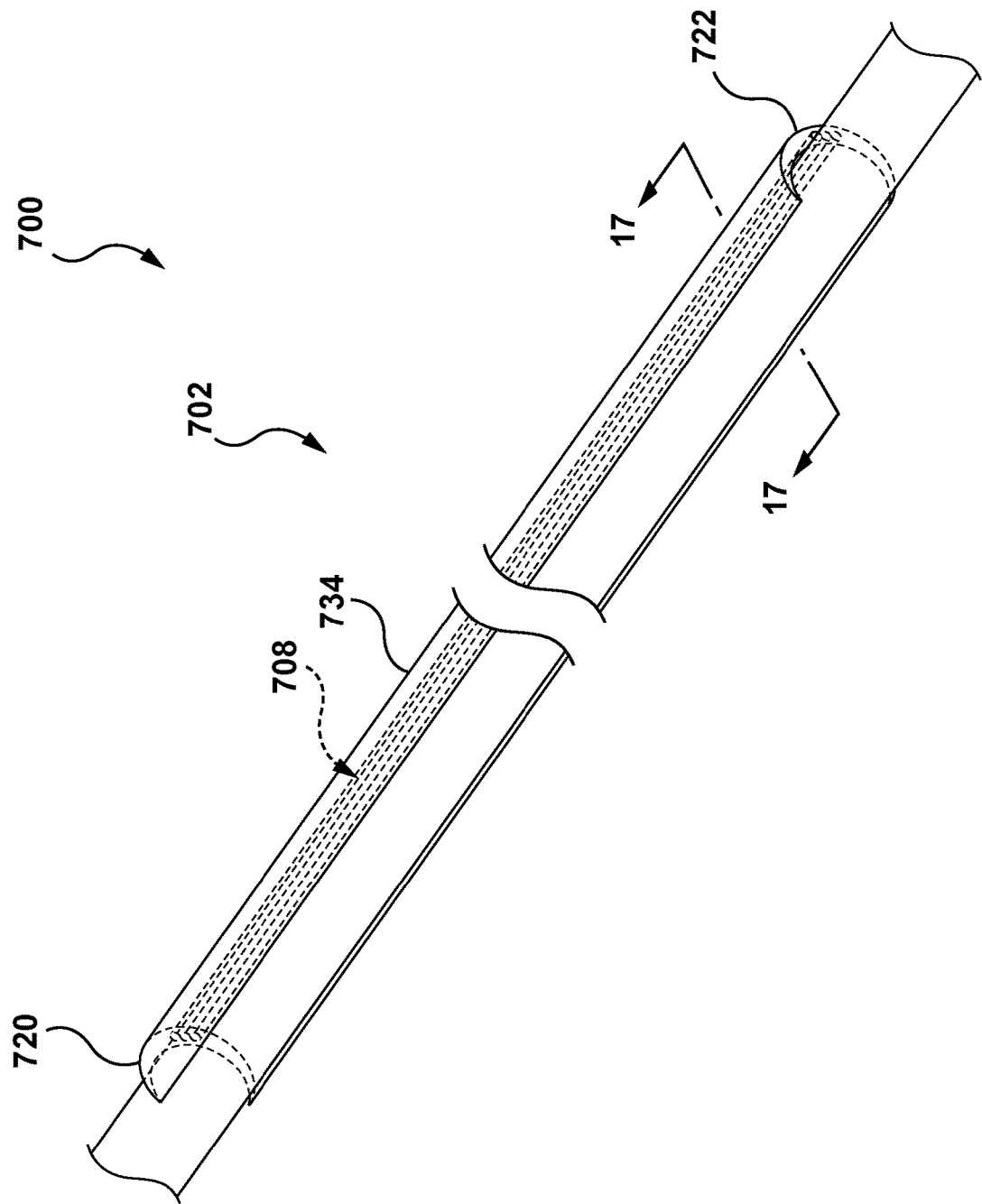
FIG. 16 is a perspective illustration of another embodiment of a proximal shaft of an FFR catheter.
Figure 18:
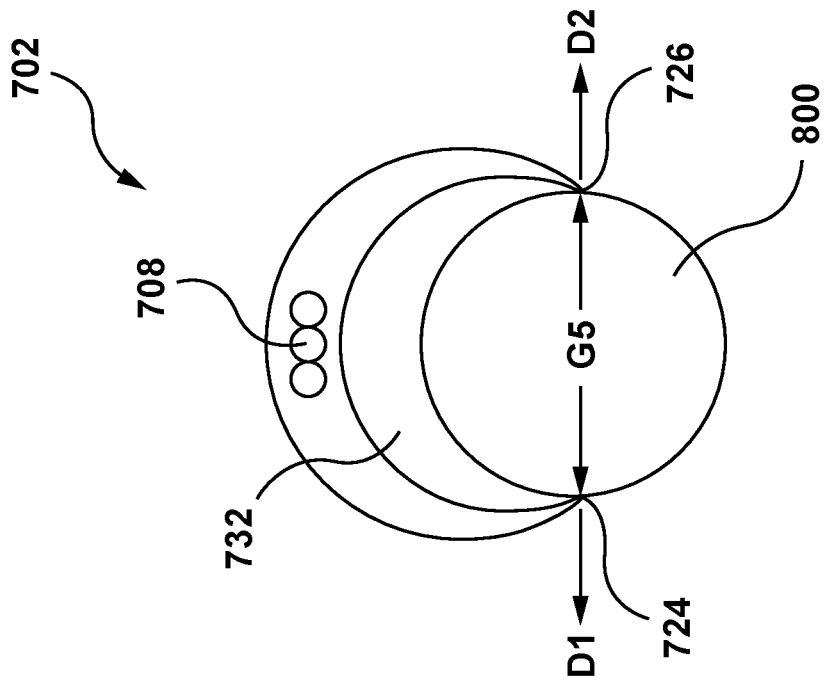
FIG. 18 is a cross-sectional illustration of the proximal shaft of FIG. 16 with a guidewire partially received therein.
Figure 17:
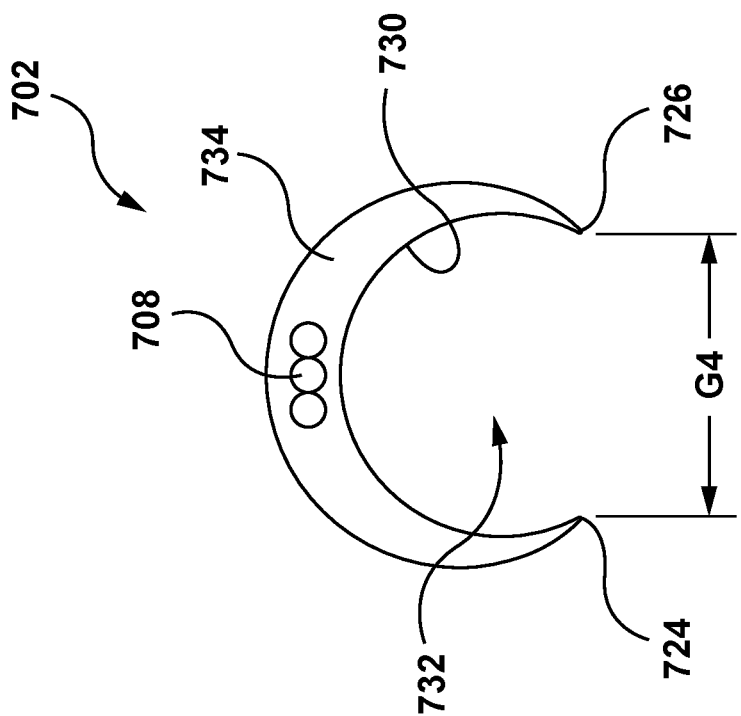
FIG. 17 is a cross-sectional illustration of the proximal shaft of FIG. 16 taken along line 17-17.
Figure 19:
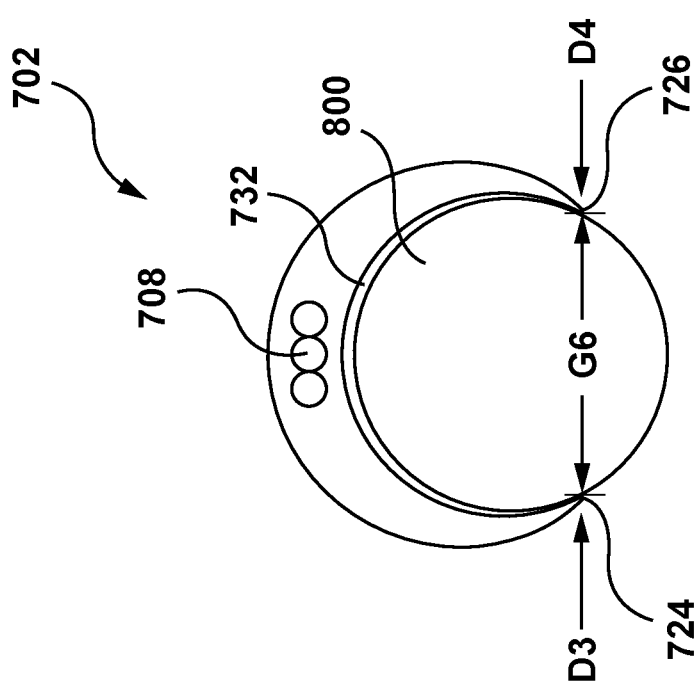
FIG. 19 is a cross-sectional illustration of the proximal shaft of FIG. 16 with the guidewire received therein.

Proximal shaft 702 extends from a proximal end 720 to a distal end 722, where proximal shaft 702 may be coupled to the distal shaft (not shown), as described with respect to FFR catheter 100. Proximal shaft 702 is similar to proximal shaft 102 in that proximal shaft 702 is substantially c-shaped in cross-section, as shown in FIGS. 17-19. Thus, in an embodiment, proximal shaft 702 includes a proximal shaft wall 734 which includes a proximal portion of pressure sensor wire(s) 708 disposed in proximal shaft wall 734, as shown in FIG. 16. In cross-section, proximal shaft wall 734 includes a first circumferential end 724, a second circumferential end 726, and a gap G4 disposed between first circumferential end 724 and second circumferential end 726, as shown in FIG. 17. An inner surface 730 of proximal shaft wall 734 defines a groove 732 for receiving guidewire 800. In an embodiment, proximal shaft wall 734 extends more than 180 degrees circumferentially from first circumferential end 724 to second circumferential end 726 along inner surface 730.

Proximal shaft 702 is configured to transition between the collapsed configuration with no guidewire received in groove 732, as shown in FIG. 17, to the transitional configuration with a guidewire 800 partially received in groove 732, as shown in FIG. 18, to the expanded configuration in which guidewire 800 is fully received in groove 732, as shown in FIG. 19. Proximal shaft 702 is configured such that as guidewire 800 is partially received within groove 732, proximal shaft 702 transitions from the collapsed configuration (FIG. 17) to the transitional configuration (FIG. 18). More specifically, as guidewire 800 is partially received within groove 732, first circumferential end 724 and second circumferential end 726 flex outwardly in a first direction D1 and a second direction D2, respectively, wherein first direction D1 is opposite second direction D2. As first circumferential end 724 and second circumferential end 726 flex outwardly, gap G4 expands in size to form a gap G5, as shown in FIG. 18, which is larger than gap G4.

As guidewire 800 is fully received within groove 732, first circumferential end 724 and second circumferential end 726 flex inwardly in a third direction D3 and a fourth direction D4, respectively, wherein third direction D3 is opposite first direction D1 and fourth direction D4 is opposite second direction D2. As the first and second circumferential ends 724, 726 move back towards each other, gap G5 shrinks back to form a gap G6, which is smaller than gap G5, but larger than gap G4. Thus, as proximal shaft 702 transitions from the transitional configuration to the expanded configuration, first circumferential end 724 and second circumferential end 726 move towards each other, as shown in FIG. 19.

Proximal shaft 702 is further configured such that upon removal of guidewire 800 received in groove 732, proximal shaft 702 transitions from the expanded configuration (FIG. 19) with guidewire 800 fully received in groove 732, to the transitional configuration (FIG. 18) with guidewire 800 partially received in groove 732, to the collapsed configuration (FIG. 17) with guidewire 800 not received in groove 732.

While proximal shaft 702 has been described herein as having a pre-set configuration (bias) to the collapsed configuration, this is not meant to limit the design, and other pre-set configurations (biases) suitable for the purposes described herein may be utilized.

Figure 20A:
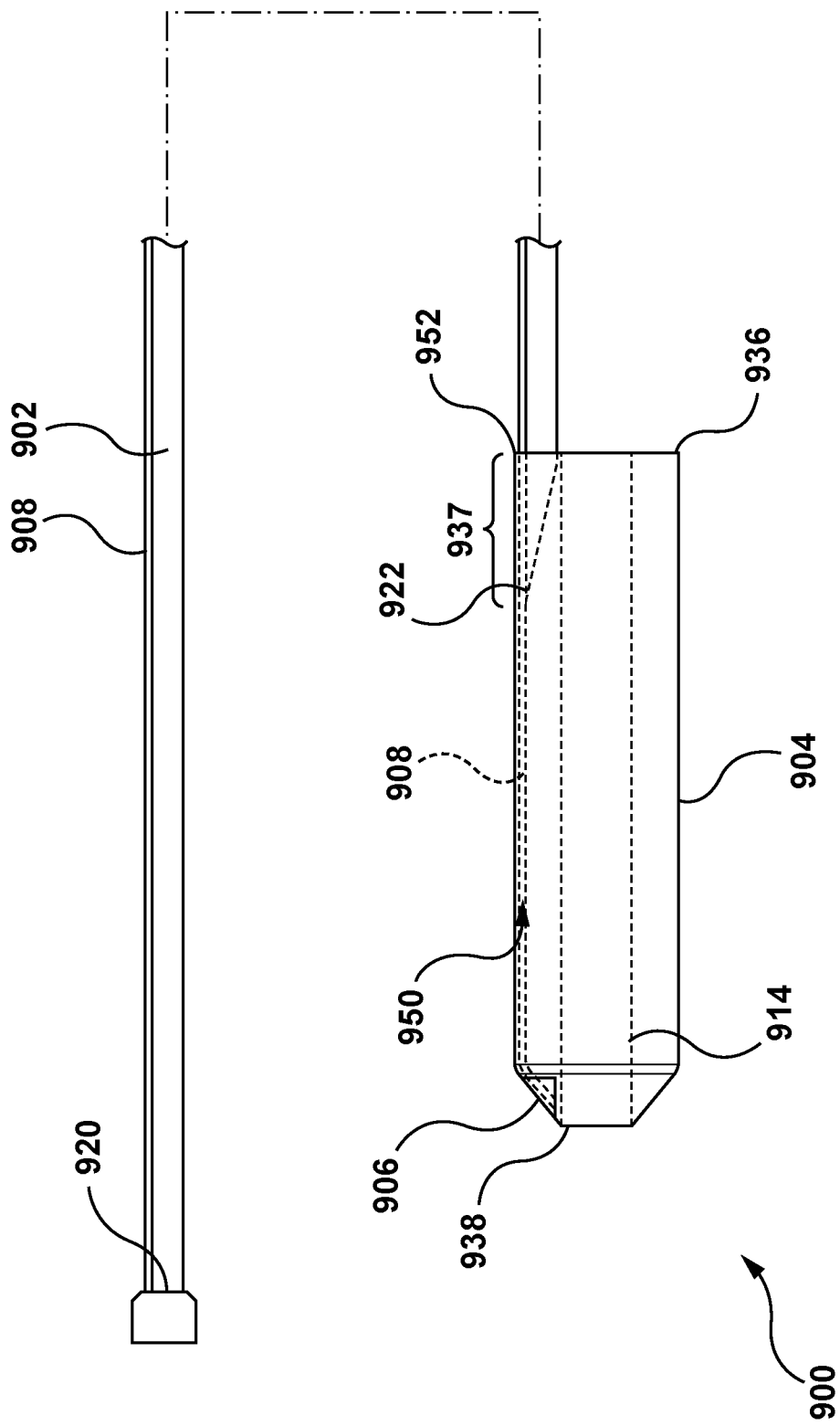
FIG. 20A is a side illustration of another embodiment of an FFR catheter.
Figure 20B:
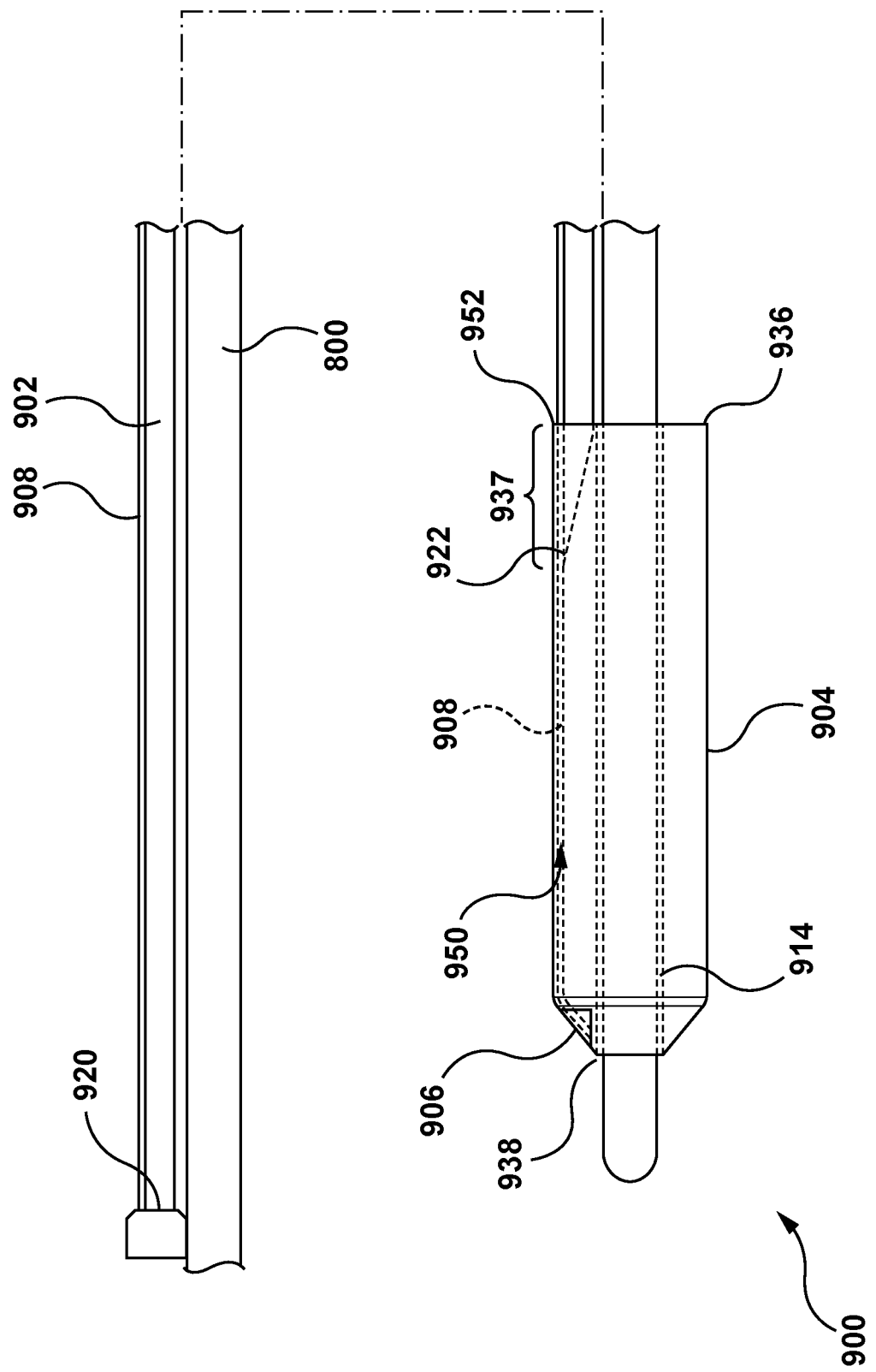
FIG. 20B is a side illustration of the FFR catheter of FIG. 20A with a guidewire received therein.
Figure 22:
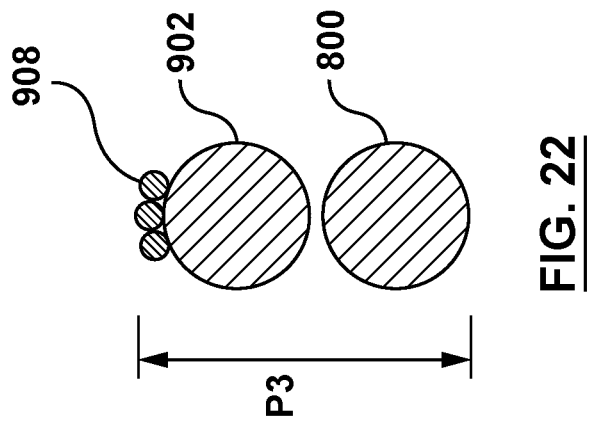
FIG. 22 is a cross-sectional illustration taken along line 22-22 of FIG. 21.
Figure 21:
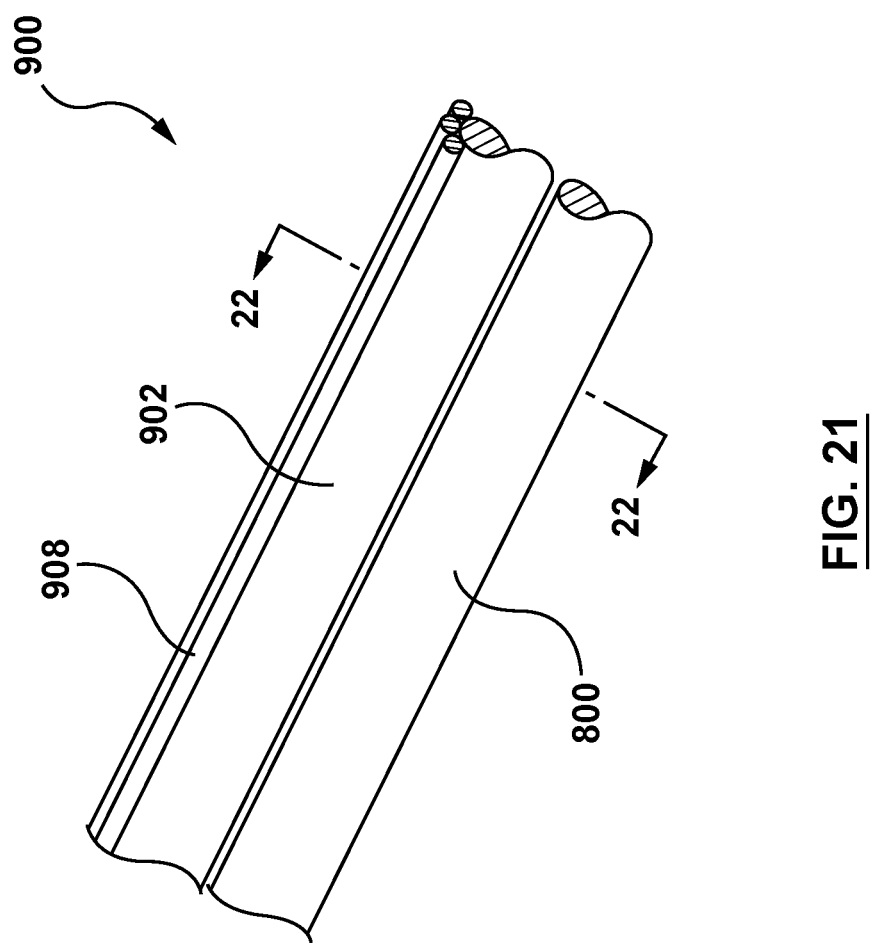
FIG. 21 is a perspective illustration of a portion of a proximal pushwire of the FFR catheter of FIG. 20A, with a guidewire disposed adjacent to the proximal pushwire.

Referring to FIGS. 20-22, an FFR catheter 900 for calculating a Fractional Flow Reserve (FFR) according to another embodiment of the present disclosure is shown. As shown in FIG. 20, FFR catheter 900 generally includes a proximal pushwire 902, a distal shaft 904 including a pressure sensor 906, and at least one pressure sensor wire 908.

Proximal pushwire 902 of FFR catheter 900 may be a cylindrical wire or elongate member, as shown in FIGS. 20-22. In particular, proximal pushwire 902 may be a solid wire, as shown in FIGS. 21-22. As a solid wire, proximal pushwire 902 may have a smaller cross-sectional profile than a hollow hypotube with similar columnar strength for pushability of FFR catheter 900. As noted above, this smaller cross-sectional profile minimizes errors in the measured proximal pressure $P_a$ during an FFR procedure. Proximal pushwire 902 may be constructed of materials such as, but not limited to, stainless steel, and other materials suitable for the purposes described herein. Proximal pushwire 902 includes a proximal end 920 and a distal end 922, as shown in FIGS. 20A-20B. As shown in FIGS. 20A and 20B, distal end 922 of proximal pushwire 902 may be tapered to provide a transition to distal shaft 904, as described in more detail below.

A proximal portion of pressure sensor wire 908 is coupled to an outer surface of proximal pushwire 902. In the embodiment shown, pressure sensor wire 908 is a tri-filar wire which is partially wrapped around proximal pushwire 902, further minimizing the cross-sectional profile of the proximal portion of FFR catheter 900 extending through a guide catheter (not shown). Pressure sensor wire 908 may be coupled to proximal pushwire 902 by, for example, and not by way of limitation, adhesives, fusing, welding, for any other method suitable for the purposes of the present disclosure. While FIGS. 20-22 show a tri-filar wire as pressure sensor wires 908, this is not meant to limit the design, and other configurations may be utilized including, but not limited to more or fewer pressure sensor wires 908.

FIG. 20A shows an embodiment of distal shaft 904 of FFR catheter 900. Distal shaft 904 includes a proximal end 936 and a distal end 938. A guidewire lumen 914 extends through distal shaft 904 and is configured to receive a guidewire 800 therein, as shown in FIG. 20B. Distal shaft 904 further defines a wire lumen 950 configured to receive at least one pressure sensor wire 908 therein. A proximal end 952 of wire lumen 950 is configured to receive and couple to tapered distal end 922 of proximal pushwire 902 therein at transition region 937, as explained in more detail below. Although FIG. 20A shows pushwire 902 disposed within proximal end 952 of wire lumen 950, this is not meant to limit the design and additional configurations maybe utilized including, but not limited to distal end 922 of proximal pushwire 902 coupled to proximal end 936 of distal shaft 904, or other configurations suitable for the purposes described herein. Distal shaft 904 may be coupled to proximal pushwire 902 by, for example, and not by way of limitation, adhesives, fusing, welding, for any other method suitable for the purposes of the present disclosure.

Distal shaft 904 is configured to extend from a proximal side of a lesion to a distal side of the lesion, such that pressure sensor 906 is disposed on the distal side of the lesion, as previously described with respect to FFR catheter 100 (FIG. 2). A distal portion of pressure sensor wire 908 is disposed within wire lumen 950 of distal shaft 904, as shown in FIG. A. 20A-20B. In an embodiment, distal shaft 904 may be 20 to 50 cm long.

Figure 23:
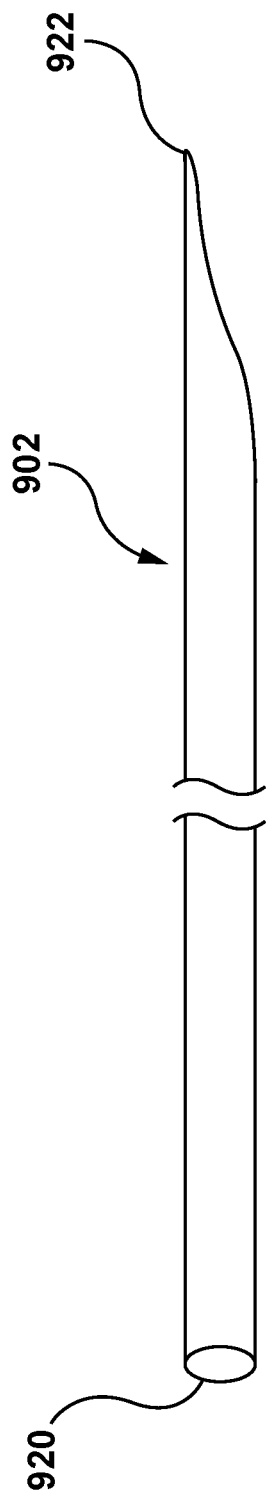
FIGS. 23-26 schematically show a method of making the FFR catheter of FIGS. 20-22.
Figure 24:
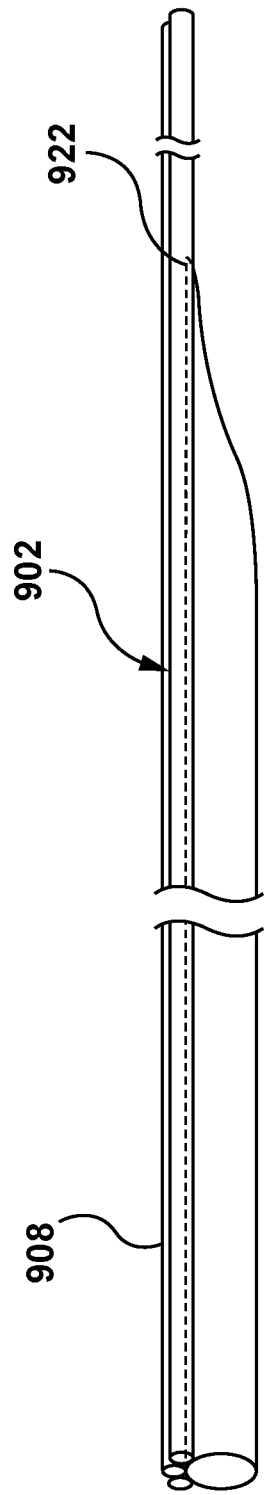

Referring to FIGS. 23-26, an embodiment of a method of making FFR catheter 900 is described. Referring to FIG. 23, proximal pushwire 902 is provided. As explained about, proximal pushwire 902 is a solid wire and distal end 922 may be tapered, as shown. Next, as shown in FIG. 24, pressure wire 908 is attached to an outer surface of proximal pushwire 902. As explained above, pressure wire 908 may be a tri-filar wire and may be attached to proximal pushwire 902 by adhesives, fusing, welding, for any other method suitable for the purposes of the present disclosure. As can be seen in FIG. 24 pressure wire 908 extends distally beyond distal end 922 of proximal pushwire 902.

Figure 25:
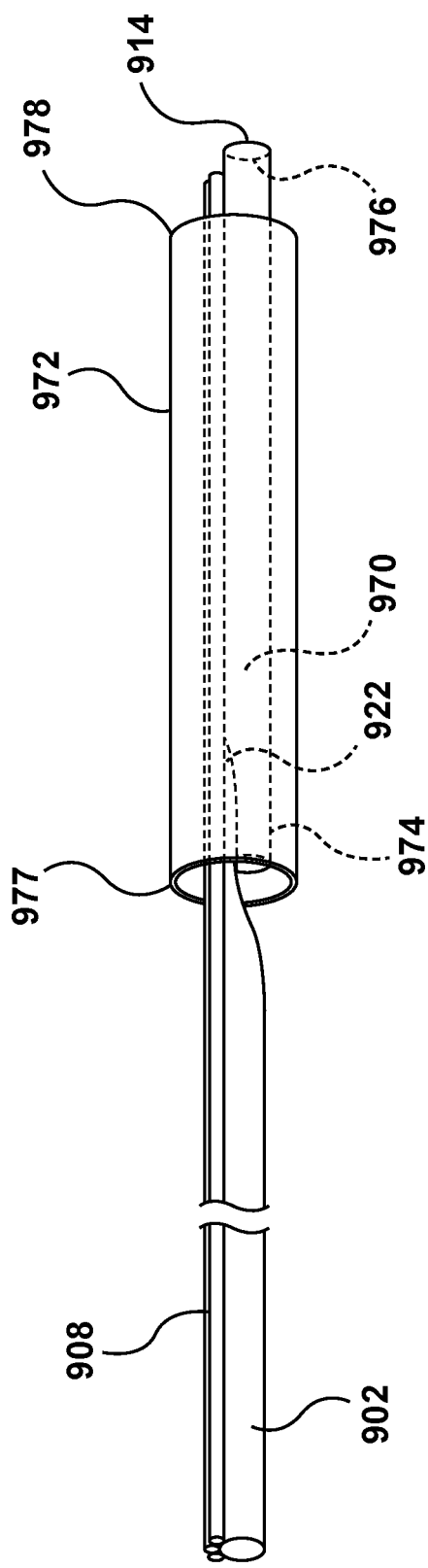
Figure 26:
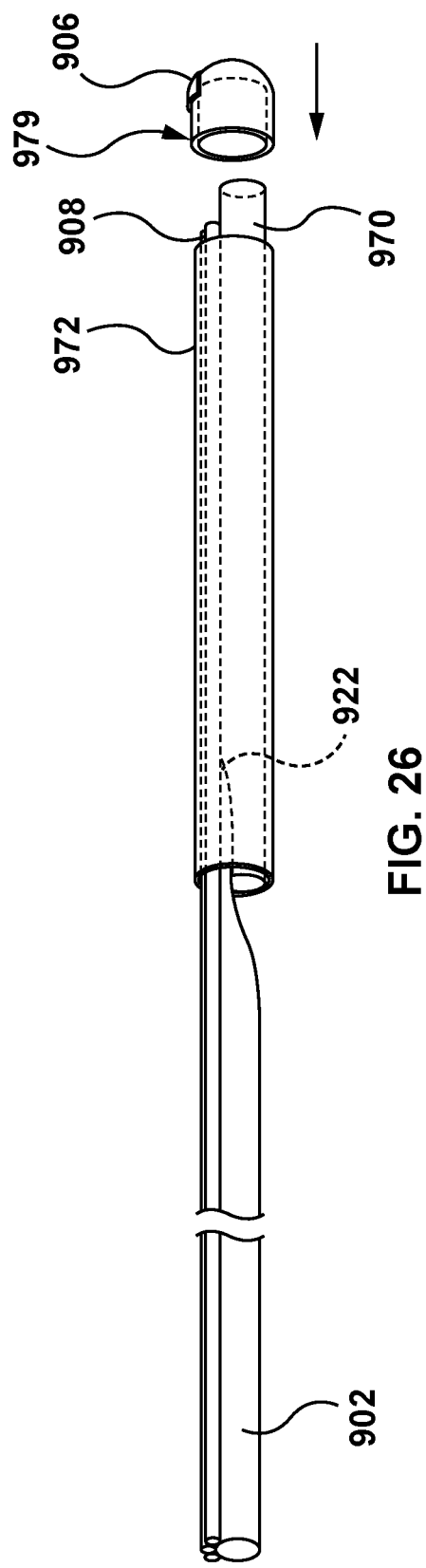

Referring to FIG. 25, a first shaft 970 having a proximal end 974 and distal end 976 is located adjacent distal end 922 of proximal pushwire 902 and adjacent the distal portion of pressure wire 908. In particular, proximal end 974 of first shaft 970 is located adjacent distal end 922 of proximal pushwire 902 and first shaft 970 extends distally such that distal end 976 of first shaft is located adjacent the distal end of pressure wire 908, as shown in FIG. 25. First shaft 970 includes guidewire lumen 914 extending from proximal end 974 to distal end 976, configured to receive guidewire 800. A second shaft 972 including a proximal end 977 and a distal end 978 is disposed around first shaft 970, distal end 922 of proximal pushwire 902, and pressure wire 908, as shown in FIG. 25. In the embodiment of FIG. 25, distal end 976 of first shaft 970 and the distal end of pressure wire 908 extend beyond distal end 978 of second shaft 972 for connection to pressure sensor 906 (FIG. 26). However, this is not meant to be limiting, and other configurations may also be used. First shaft 970 may be made from conventional catheter materials, such as, but not limited to, polyamide, polyethylene and PEBA and/or combinations thereof, either blended or co-extruded. Second shaft 972 may be a heat shrink tube formed from a polymer, such as, but not limited to, polyurethane, fluorinated ethylene-propylene, tetrafluoroethylene and polyesters. As shown in FIG. 25, second shaft 972 is in the form of a tube that fits loosely over first shaft 970, pressure wire 908, and distal end 922 of proximal pushwire 102. Once heated, second shaft 972 shrinks to tightly fit against the outer surface of first shaft 970, pressure wire 908, and distal end 922 of proximal pushwire 902, as shown in FIG. 26.

With second shaft 972 shrunk over first shaft 970, a distal tip 979 with pressure sensor 906 coupled thereto may be provided over distal end 976 of first shaft 970 and coupled thereto. The distal end of pressure wire 908 is coupled to pressure sensor 906, resulting in FFR catheter 900 of FIG. 21. The method is shown with a separate distal tip 979 coupled to first shaft 970. However, this is not meant to be limiting and other methods may be used. For example, pressure sensor 906 may be attached to a distal portion of first shaft 970. When first shaft 970 is provided adjacent to pressure wire 908, pressure wire 908 may be coupled to pressure sensor 906. Second shaft 972 may then be provided over first shaft 970 and pressure sensor wire 908. Other methods and constructions may also be utilized suitable for the purposes of the present disclosure.

While only some embodiments according to the present invention have been described herein, above, it should be understood that they have been presented by way of illustration and example only, and not limitation. Various changes in form and detail can be made therein without departing from the spirit and scope of the invention. Further, each feature of each embodiment discussed herein can be used in combination with the features of any other embodiment. All patents and publications discussed herein are incorporated by reference herein in their entirety.

What is claimed is:
1. A catheter comprising:
 a proximal shaft, wherein the proximal shaft is substantially C-shaped such that, in cross-section, the proximal shaft includes a first circumferential end, a second circumferential end, and a gap between the first circumferential end and the second circumferential end, the proximal shaft defining a groove configured to receive a guidewire therein such that when the guidewire is disposed within the groove, a portion of the guidewire is disposed in the gap between the first circumferential end and the second circumferential end such that the gap in a collapsed configuration of the proximal shaft without the guidewire disposed in the groove is a first size and the gap in an expanded configuration of the proximal shaft with the guidewire fully disposed in the groove is a second size larger than the first size;
 a distal shaft coupled to the proximal shaft, wherein the distal shaft defines a guidewire lumen therein, wherein the guidewire lumen is configured to receive the guidewire therein;
 a pressure sensor coupled to the distal shaft; and
 a pressure sensor wire operably connected to the pressure sensor, wherein a proximal portion of the pressure sensor wire is disposed within a proximal shaft wall of the proximal shaft and a distal portion of the pressure sensor wire is disposed within a distal shaft wall of the distal shaft,
 wherein the proximal shaft is substantially C-shaped from a proximal end of the proximal shaft to the distal shaft.
2. The catheter of claim 1, wherein the groove is defined by an inner surface of the proximal shaft extending from the first circumferential end to the second circumferential end.
3. The catheter of claim 2, wherein the inner surface includes a lubricious coating.

4. The catheter of claim 1, further comprising:
a plurality of bands extending around an outer surface of the proximal shaft and configured to extend around an outer surface of the guidewire received in the groove.

5. The catheter of claim 1, wherein the proximal shaft further includes a cover coupled to an outer surface of the proximal shaft.

6. The catheter of claim 5, wherein the cover is configured to extend circumferentially around the outer surface of the proximal shaft and an outer surface of the guidewire received in the groove.

7. The catheter of claim 5, wherein the cover is configured to extend around the outer surface of the proximal shaft and extend around a portion of an outer surface of the guidewire received in the groove.

8. The catheter of claim 5, wherein the cover is substantially c-shaped and faces an opposite direction in cross-section as the substantially c-shaped proximal shaft, wherein a first circumferential end of the cover is coupled to the first circumferential end of the proximal shaft, a second circumferential end of the cover is coupled to the second circumferential end of the proximal shaft, and the cover extends over the groove such that the cover is configured to extend around an outer surface of the guidewire received in the groove.

9. The catheter of claim 1, wherein the proximal shaft extends circumferentially more than 180 degrees from the first circumferential end to the second circumferential end along an inner surface of the proximal shaft.

10. The catheter of claim 9, wherein the first circumferential end and the second circumferential end are configured to flex outwardly to receive the guidewire in the groove.

11. The catheter of claim 1, wherein the catheter is a micro-catheter.

12. A catheter comprising:
a proximal shaft, wherein the proximal shaft is substantially C-shaped such that, in cross-section, the proximal shaft includes a first circumferential end, a second circumferential end, and a gap between the first circumferential end and the second circumferential end, the proximal shaft defining a groove configured to receive a guidewire therein, wherein the proximal shaft extends more than 180 degrees from the first circumferential end to the second circumferential end along an inner surface of the proximal shaft, and wherein the gap in a collapsed configuration of the proximal shaft without the guidewire disposed in the groove is a first size and the gap in an expanded configuration of the proximal shaft with the guidewire disposed in the groove is a second size larger than the first size;
a distal shaft coupled to the proximal shaft, wherein the distal shaft defines a guidewire lumen therein, wherein the guidewire lumen is configured to receive the guidewire therein;
a pressure sensor coupled to the distal shaft; and
a pressure sensor wire operably connected to the pressure sensor, wherein a proximal portion of the pressure sensor wire is disposed within a proximal shaft wall of the proximal shaft and a distal portion of the pressure sensor wire is disposed within a distal shaft wall of the distal shaft,
wherein the proximal shaft extends to a proximal end of the catheter such that the proximal shaft is substantially C-shaped from the proximal end of the catheter to the distal shaft.

13. The catheter of claim 12, wherein the groove is defined by the inner surface of the proximal shaft extending from the first circumferential end to the second circumferential end.

14. The catheter of claim 13, wherein the inner surface includes a lubricious coating.

15. The catheter of claim 12, wherein the gap in a transitional configuration of the proximal shaft with the guidewire partially disposed within the groove is a third size larger than the first size and the second size.

16. The catheter of claim 12, wherein the catheter is a micro-catheter.

* * * * *